(12) United States Patent
Singh et al.

(10) Patent No.: US 8,318,954 B2
(45) Date of Patent: Nov. 27, 2012

(54) CLEAVABLE CARNITINE COMPOUND

(75) Inventors: Inder Pal Singh, Edmonton (CA);
Shradha Singh, Edmonton (CA);
Antoine Noujiam, Edmonton (CA);
Bruce D. Hirsche, legal representative, Edmonton (CA); David S. Tam, Edmonton (CA)

(73) Assignee: Nou Life Sciences, Inc., Edmonton, AB (CA)

( * ) Notice: Subject to any disclaimer, the term of this patent is extended or adjusted under 35 U.S.C. 154(b) by 677 days.

(21) Appl. No.: 12/280,572

(22) PCT Filed: Feb. 23, 2007

(86) PCT No.: PCT/CA2007/000302
§ 371 (c)(1),
(2), (4) Date: Aug. 18, 2009

(87) PCT Pub. No.: WO2007/095760
PCT Pub. Date: Aug. 30, 2007

(65) Prior Publication Data
US 2009/0312404 A1    Dec. 17, 2009

Related U.S. Application Data

(60) Provisional application No. 60/775,867, filed on Feb. 23, 2006.

(51) Int. Cl.
*C07D 339/04* (2006.01)
(52) U.S. Cl. .......................................................... 549/39
(58) Field of Classification Search ..................... 549/39
See application file for complete search history.

(56) References Cited

FOREIGN PATENT DOCUMENTS
WO          00/11967       *  3/2000
* cited by examiner

*Primary Examiner* — Taofiq A Solola
(74) *Attorney, Agent, or Firm* — J. Jay Haugen; William J. Bundren

(57) ABSTRACT

The invention includes novel compounds, including but not limited to formula A and formula B, and an improved delivery method. These compounds and methods are useful in preventing or treating diseases or conditions associated with or caused by the presence of free radicals, and are useful for increasing cellular metabolism while simultaneously alleviating the resultant increase in oxidative stress. Specifically, a carnitine is bound to a lipoic acid derivative or to dihydrolipoic acid or its derivatives using a hydrolysable linker to form a single compound.

5 Claims, 12 Drawing Sheets

Dihydrolipoic Acid

Lipoic Acid + N- Acetyl Carnitine HCL

Lipoic Acid + N- Acetyl Carnitine HCL

Lipoic Acid + N- Acetyl Carnitine HCL

CLEAVABLE CARNITINE COMPOUND

I. FIELD OF THE INVENTION

The field of invention is compounds and methods of delivering molecules via such compounds for preventing or treating diseases associated with the presence of free radicals in mammals or for increasing cellular metabolism while simultaneously alleviating oxidative stress.

II. BACKGROUND OF THE INVENTION

Mitochondria are the organelles of cellular respiration. Carnitine transports fatty acids into mitochondria as fuel and is involved in energy production. Once in the mitochondria fatty acid chains are broken into two-carbon acetyl-CoA units (a process known as β-oxidation), acetyl-CoA can be converted to ATP via the citric acid cycle and oxidative phosphorylation.

Cardiolipin is a component of the mitochondrial membrane and is involved in maintaining mitochondria membrane potential and mitochondrial activity, particularly at the level of fatty acid, β-oxidation processes.

Free radicals are molecules containing unpaired electrons. These unpaired electrons cause oxidative damage in cells and are passed from molecule to molecule turning the recipient into a free radical and neutralizing the donor. In the case of lipid peroxidation, there is a chain reaction which involves both damage and passing of radicals.

Cellular macromolecules are vulnerable to free radical damage: lipids, proteins and nucleic acids can all be damaged. Free radical damage contributes to: cardiovascular disease, cancer, neurodegenerative diseases, inflammatory diseases and other age related degenerative diseases.

Mitochondria are a major source of free radicals and much free radical damage occurs to mitochondrial membranes and mitochondrial DNA due to the mitochondria's own oxidation by products. Mitochondria decay with cellular aging (Shigenaga et. al. 1994, PNAS 91, 10771). Mitochondrial decay is accompanied by a reduction in cardiolipin levels and an increase in free radicals and harms all cellular processes.

Administration of the acetylated version of carnitine, acetyl-L-carnitine, and restores normal cardiolipin concentration in the mitochondria and reactivates mitochondrial activity, including the fatty aid β-oxidation processes. Acetyl L-carnitine also enhances mitochondrial activity by promoting the utilization of the glycolytic pathway for ATP production.

Acetyl L-carnitine can be used to help prevent neuronal lesions or chronic neuronal degeneration; to protect cerebral tissue from damaging peroxidative events; to treat muscular functional deficits and also in the regulation of insulin activity (Patent PCT/IT99/00268 Antioxidant composition comprising acetyl L-carnitine and alpha-lipoic acid).

Carnitine and carnitine derivatives have been used as metabolites for animals and for human diet and therapy: U.S. Pat. No. 4,687,782 (Nutritional composition for enhancing skeletal muscle adaptation to exercise training); U.S. Pat. No. 4,343,816 (Pharmaceutical composition comprising an acyl-carnitine, for treating peripheral vascular diseases); U.S. Pat. No. 5,560,928 (Nutritional and/or dietary composition and method of using the same); U.S. Pat. No. 5,504,072 (Enteral nutritional composition having balanced amino acid profile); U.S. Pat. No. 5,391,550 (Compositions of matter and methods for increasing intracellular ATP levels and physical performance levels and for increasing the rate of wound repair); U.S. Pat. No. 5,240,961 (Method of treating reduced insulin-like growth factor and bone loss associated with aging).

Carnitine is studied extensively in part because of the important role it plays in fatty acid oxidation and energy production, and because it is a well-tolerated and generally safe therapeutic agent. It is proven treatment in children who have recessive defects in the carnitine transporter system and in individuals treated with pivalate containing antibiotics. Other benefits attributed to carnitine result from the management of secondary carnitine deficiencies. These benefits are supported by preliminary findings and need to be confirmed through well-controlled randomized trials. While there is agreement on carnitine's role as a prescription product for the treatment of primary carnitine deficiencies, its benefits as a dietary supplement in individuals who are carnitine sufficient is debated.

Carnitine is termed a conditionally essential nutrient, as under certain conditions its requirements may exceed the individual's capacity to synthesize it. Carnitine mediates the transport of medium/long-chain fatty acids across mitochondrial membranes, facilitating their oxidation with subsequent energy production; in addition, it facilitates the transport of intermediate toxic compounds out of the mitochondria preventing their accumulation. Because of these key functions, carnitine is concentrated in tissues that utilize fatty acids as their primary dietary fuel, such as skeletal and cardiac (heart) muscle. Dietary sources of carnitine include foods of animal origin, such as meat and dairy products. In general, healthy adults do not require dietary carnitine as carnitine stores are replenished through endogenous synthesis from lysine and methionine in the liver and kidneys. Excess carnitine is excreted via the kidneys. In the US, carnitine is an approved prescription drug for the treatment of primary systemic carnitine deficiency and secondary carnitine deficiency syndromes. Carnitine is also available over-the-counter as a dietary supplement, as an aid to weight loss, to improve exercise performance, and to enhance a sense of well-being.

Carnitine is also used for the following treatments and determinations: 1) the treatment of non-alcoholic steatohepatitis (NASH). Steatohepatitis or fat deposits in the liver can result from obesity, diabetes, long-term use of steroids and the antibiotic tetracycline 2) Identifying the specific acylcarnitine that accumulates in peripheral arterial disease in order to determine the specific metabolic disruption. Patients with peripheral arterial disease, who become symptomatic with claudication, have a marked impairment in exercise performance and overall functional capacity. 3) Determining the benefits of carnitine supplementation in the prevention of osteoporosis in post-menopausal women who depend on life-long thyroid stimulating hormone (TSH)-suppressive L-T4 therapy for the management of thyroid cancer. 4) Determining the benefits of carnitine supplementation as prophylaxis or ancillary therapy of serious hyperthyroidism in elderly patients on the anti-arrhythmic drug amiodarone. 5) Determining whether carnitine supplementation can improve symptoms other than fatigue in cancer patients. In addition, test the interaction between carnitine and anti-neoplastics agents used in cancer treatment.

Alpha-lipoic acid: Although Acetyl L-carnitine may improve mitochondrial function, it may also increase free radical damage due to increased energy production through oxidative phosphorylation. So combining Acetyl L-carnitine and a separate antioxidant, such as lipoic acid, can provide both improved metabolic function and reduced oxidative stress (Patent PCT/US98/12545 Dietary Composition for Enhancing Metabolism and Alleviating Oxidative stress.)

Alpha-lipoic acid and some of its metabolites are active antioxidants in the mitochondria. Lipoic acid is an endogenous co-factor for mitochondrial alpha-keto acid dehydrogenase, which may aid in cellular glucose-dependent ATP production. Lipoic acid also increases intracellular ascorbate and glutathione levels. The antioxidant effect of alpha-lipoic acid may be either direct, as an antioxidant itself, or indirect, via restoration of glutathione and ascorbic acid concentrations.

As described in Patent PCT/IT99/00268, alpha-lipoic acid helps in the prevention of diabetic neuropathies and has neuro-protective capability. Those skilled in the art know that administering Alpha-lipoic acid is effective for treating lipid peroxidation (including neural lesions), diabetic neuropathy, glycosylation/glucose oxidation reactions. Alpha lipoic acid may help prevent diabetes related diseases, by inhibiting the activation of the nuclear transcription factor (NF-kB) by reactive oxygen species which in turn, inhibits the associated cascade of neurotoxic and cytotoxic factors. Many of the complications associated with diabetes, such as neuropathies and ocular cataracts are mediated by reactive oxygen species.

Alpha-lipoic acid inhibits the aldose reductase activated by hyperglycemia, enhances insulin-induced muscular utilization of glucose and, in diabetic subjects, and reduces resistance to the effects of insulin on glucose. The action of alpha-lipoic acid on carbohydrate metabolism is due essentially to its ability to act as a coenzyme in the oxidative decarbohydroxylation of pyruvate and other alpha-ketoacids and, through the acetates, in the activation of the tricarboxylic acid cycle leading to the formation of ATP.

A protective effect of alpha-lipoic acid has also been observed in pancreatic cells placed in contact with inflammatory agents.

Lipoic acid has been used as human nutritional supplement and in dietary prophylaxis and therapy. See, for example, U.S. Pat. Nos. 5,607,980 (Topical compositions having improved skin); 5,472,698 (Composition for enhancing lipid production in skin); 5,292,538 (Improved sustained energy and anabolic composition and method of making); 5,536,645 (Nutritive medium for the culture of microorganisms); and 5,326,699 (Serum-free medium for culturing animal cells).

Supplementation with both lipoid acid and acetyl-l-carnitine is an effective way of improving mitochondrial metabolic function without increasing oxidative stress [PROCEEDINGS OF THE NATIONAL ACADEMY OF SCIENCES (USA); Hagen, T; 99(4):1870-1875 (2002)]. ALCAR supplementation in combination with lipoic acid substantially restored spatial memory capacity in experimental rats [PROCEEDINGS OF THE NATIONAL ACADEMY OF SCIENCES (USA); Liu, J; 99(4):2356-2361 (2002)].

Lipoic acid can be obtained in the diet from foods containing high metabolic activity. Meat from heart can contain ten times the amount of lipoic acid as meat from muscle. Spinach is also rich in lipoic acid. Lipoic acid is readily digested, absorbed and transported to tissues. Lipoic acid induces cystine/cysteine uptake, thereby increasing synthesis of glutathione.

Patent PCT/IT99/00268 discloses that a composition comprising acetyl L-carnitine and alpha-lipoic acid is effective in the prevention and/or treatment of tissue damage induced by the presence of free radicals due to environmental pollution; of cerebral or myocardial lesions induced by free radicals after cerebral or myocardial ischemia and as a result of reperfusion; of toxic or diabetic neuropathies, and of metabolic disorders in the glucose utilization.

Either acetyl L-carnitine or alpha-lipoic acid can be used on its own in treating neuropathies or in helping to prevent toxic and metabolic damage, as well as in helping to prevent the neuronal lesions arising from such damage. However, Acetyl L-carnitine and alpha-lipoic acid have a more powerful effect when used together in combination. In particular, Patent PCT/IT99/00268 showed that the combination:

(a) had neuroprotective activity in a cerebral ischemia model. Lesions due to cerebral ischemia are related to the production of free radicals and of nitrous oxide. The combination protected against the toxic action of free radicals and reduced the ischemic area. In view of its antioxidant capability, this composition is also indicated in the prevention or treatment of abnormalities of toxic or anoxic origin related to the release of free radicals in other organs and tissues;

(b) helped control serum glucose in hyperglycemia induced rats, hyperglycemia being one cause of diabetic disease at neural, muscular and endothelial level;

(c) reduced the accumulation of intracellular sorbitol, excess sorbitol being associated with lesions induced by diabetic hyperglycemia;

(d) potentiated the neurotrophic effect of Insulin-like growth factor-1 in vitro, suggesting a potential benefit to pathological abnormalities related to ageing, such as neurodegenerative disorders;

(e) improved neuromuscular conduction velocity and muscular contraction force in diabetic rats;

(f) improved motor co-ordination in "wobbler mice", which have a phenotype involving progressive atrophy of motoneurons and musculo-cutaneous nerve fibres;

(f) accelerated regeneration of the sciatic nerve in diabetic rats; and (g) helped protect sensory neurons from Cisplatin induced lesions.

Patent PCT/US98/12545 discloses a method of increasing the metabolic rate of aged cells of a rodent host without a concomitant increase in metabolic production of reactive oxygen species. This method involved orally administering a composition of carnitine and of acetyl-L-carnitine of sufficient concentration to increase cellular metabolic process while simultaneously alleviating the resultant increase in oxidative stress. The treated animal showed host cell mitochondria with enhanced levels of cardiolipin and membrane potential, reduced production of reactive oxygen species, and mitigation of indicia of aging, including activity, muscle tone, coat appearance and kidney morphology.

Although patents PCT/IT99/00268 and PCT/US98/12545 teach use of acetyl L-carnitine and alpha-lipoic acid in combination, neither provides acetyl L-carnitine and alpha-lipoic acid in a single compound. No prior art provides acetyl L-carnitine and alpha-lipoic acid (or an alpha-lipoic acid derivative) linked to each other in a single compound by a linker that is hydrolysable intracellularly at the active site.

Further, the prior art generally contemplates administering compositions of acetyl L-carnitine or alpha-lipoic acid systemically.

All publications and patent applications cited in this specification are herein incorporated by reference as if each individual publication or patent application were specifically and individually indicated to be incorporated by reference. Although the present invention has been described in some detail by way of illustration and example for purposes of clarity of understanding, it will be apparent to those of ordinary skill in the art, in light of the teachings of this invention, that certain changes and modifications may be made thereto without departing from the spirit or scope of any appended claims.

III. SUMMARY OF THE INVENTION

The present invention provides a novel compound comprising L-carnitine linked or bonded to a lipoic acid, and methods of using one or more of these compounds for treating mammals including humans for any disease or condition associated with the presence of free radicals. In some embodiments of the invention, the presence of free radicals comprises the accumulation of free radicals in cells, typically due to toxic, anoxic, or metabolic causes. Some embodiments of the invention include a novel compound and an improved delivery method for use in increasing cellular metabolism while simultaneously alleviating the resultant increase in oxidative stress.

The compounds of the present invention, Lipoic acid/Carnitine conjugates (LC conjugates) may be used to treat any disease or condition for which it is beneficial to administer Lipoic acid or Carnitine individually.

Lipoic acid has been given for mushroom poisoning, heavy metal intoxication and diabetic neuropathy. The anti-glycation capacity of lipoic acid combined with its capacity for hydrophobic binding enables lipoic acid to prevent glycosylation of albumin in the bloodstream. Lipoic acid is known to biochemists as being part of a prosthetic group (lipoamide) of the dihydrolipoamide acetyltransferase portion of the pyruvate dehydrogenase enzyme complex that converts pyruvate to Acetyl-CoA prior to entry into the citric acid cycle.

Even small amounts of cadmium ($Cd^{2+}$) can cause significant lipid peroxidation in the brain, which can be prevented by lipoic acid [FREE RADICAL BIOLOGY & MEDICINE; Packer, L; 22(1/2):359-378 (1997)]. Lipoic acid (DHLA) chelation of iron and copper in the brain may reduce free-radical damage contributing to Alzheimer's disease [NEUROBIOLOGY OF AGING 23:1031-1038 (2002)]. Lipoic acid has been shown to protect against age-related increase in InterLeukin-1 (IL-1)β: concentration possibly related to an age-related decline in arachidonic acid in the hippocampus causing impaired LTP and glutamate release [NEUROBIOLOGY OF AGING; McGahon, B M; 20:655-664 (1999)].

Lipoic acid is also beneficial in reducing ischemic-reperfusion injury by direct action as well as by glutathione protection and xanthine oxidase inhibition [FREE RADICAL BIOLOGY & MEDICINE; Packer, L.; 19(2):227-250 (1995)]. Protection against peroxynitrite damage by lipoic acid is highly dependent upon the target molecule [JOURNAL OF BIOLOGICAL CHEMISTRY; Rezk, B M; 279(11): 9693-9697 (2004)]. Protection of neurons from glutamate excitotoxicity is equally effective by the R-form and S-form [FREE RADICAL BIOLOGY & MEDICINE; Tirash, O; 26(11/12):1415-1426 (1999)].

In mitochondria, lipoic acid can compensate for the low concentrations of glutathione in that organelle, and can chelate heavy metal ions that could generate free radicals. In old rats supplemented with R-lipoic acid, mitochondrial membrane potentials and oxygen consumption have been restored significantly while at the same time MDA (MalonDiAldehyde, a product of lipid peroxidation) was reduced to one-fifth of the unsupplemented level [FASEB JOURNAL; Hagen, T M; 13(2):411-418 (1999)]. Age-related damage to heart muscle cell mitochondria has been considerably reduced by lipoic acid supplementation [FASEB JOURNAL; Suh, J H; 15(3):700-706 (2001)]. Glutathione synthesis declines considerably with age, but lipoic acid has also been shown to restore glutathione synthesis to more youthful levels in aging rat liver [PROCEEDINGS OF THE NATIONAL ACADEMY OF SCIENCES (USA); Suh, J H; 101(10):3381-3386 (2004)].

IV. BRIEF DESCRIPTION OF THE FIGURES

V. DETAILED DESCRIPTION OF THE INVENTION

Figure 1:
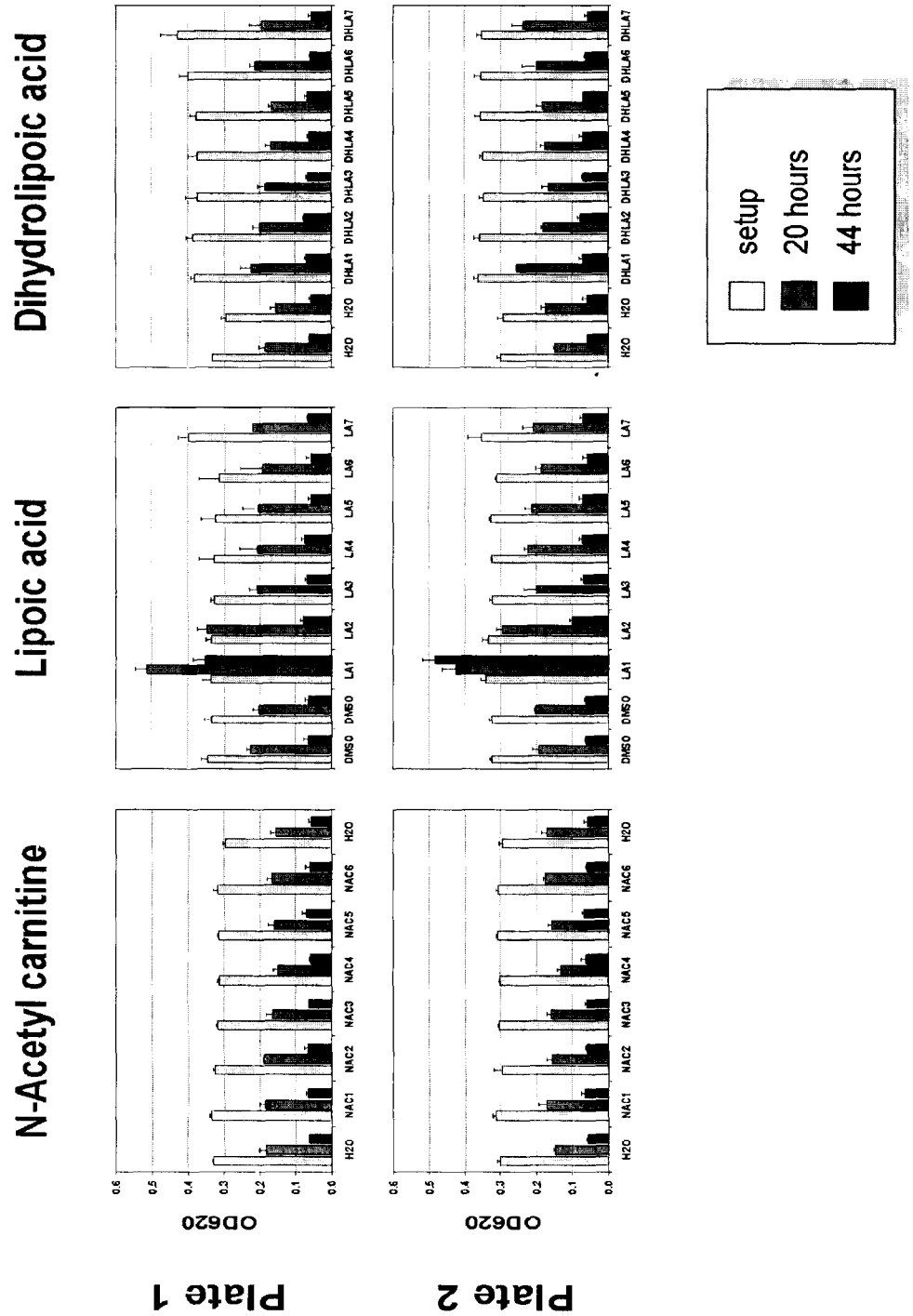
FIG. 1 shows the results of the toxicity tests described in Example 4.
Figure 2:
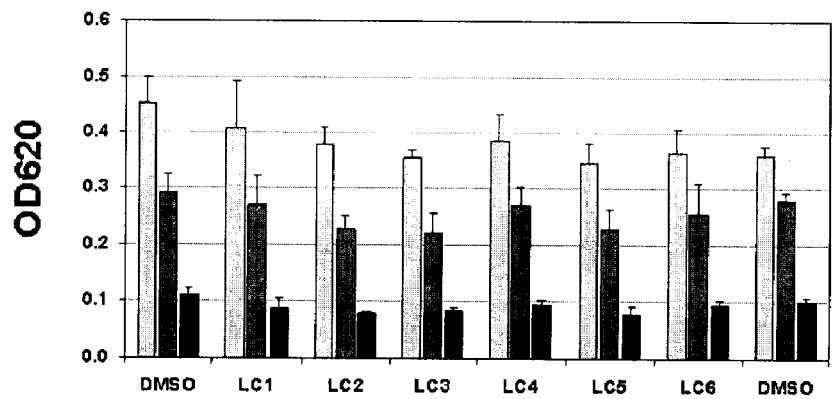
FIG. 2 shows the results of the toxicity tests described in Example 5.
Figure 2:
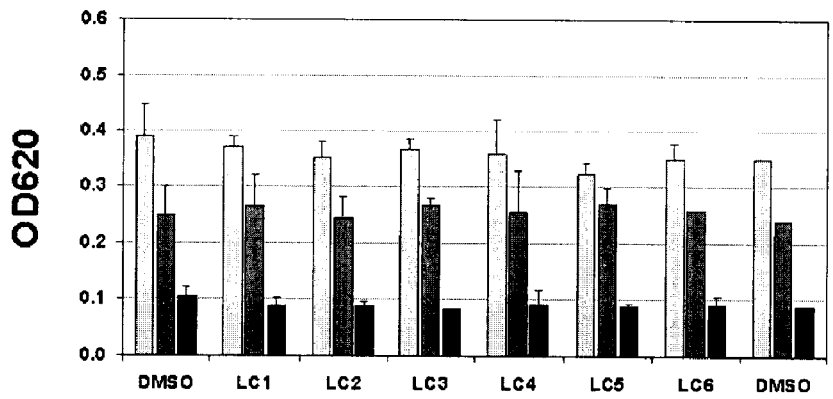
Figure 2:
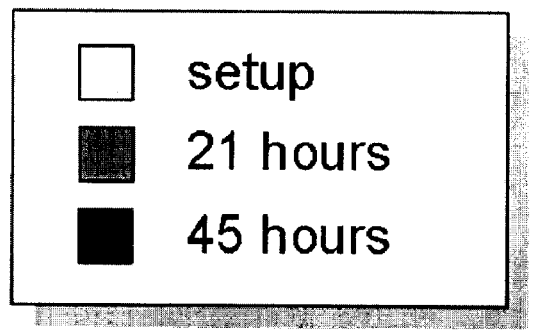
Figure 3:
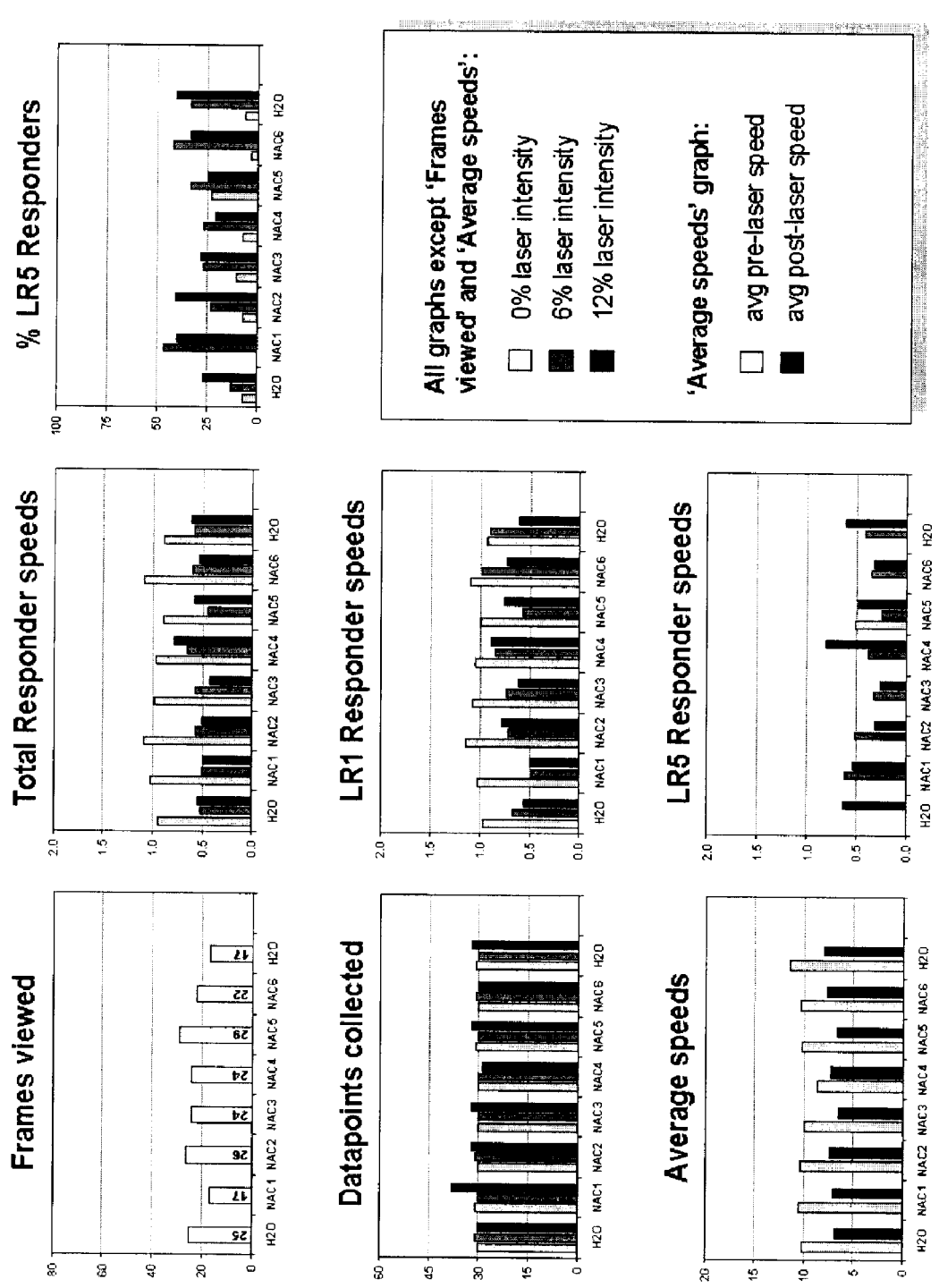
FIG. 3 shows the results of the dose response tests for carnitine described in Example 6.
Figure 4:
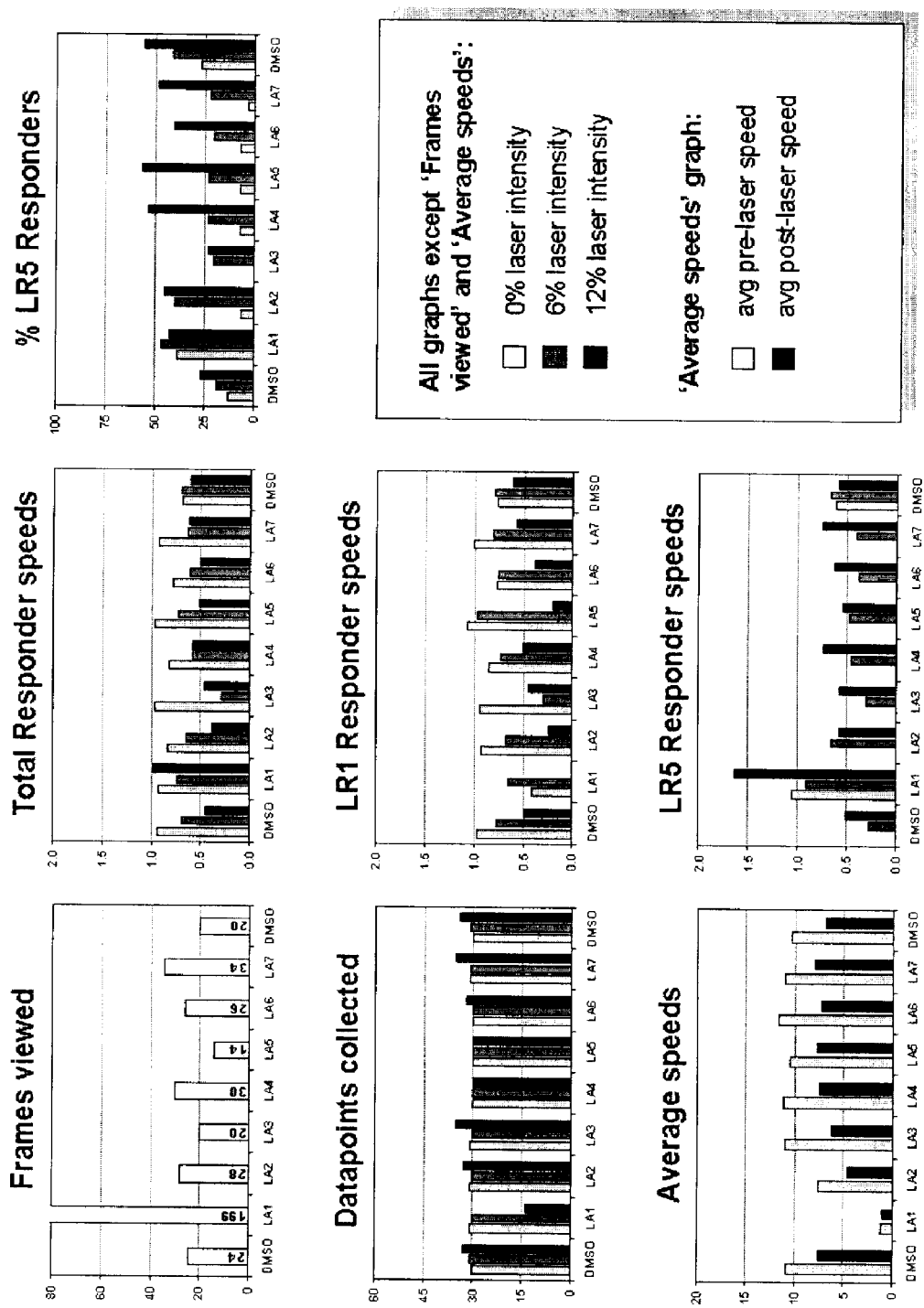
FIG. 4 shows the results of the dose response tests for lipoic acid described in Example 6.
Figure 5:
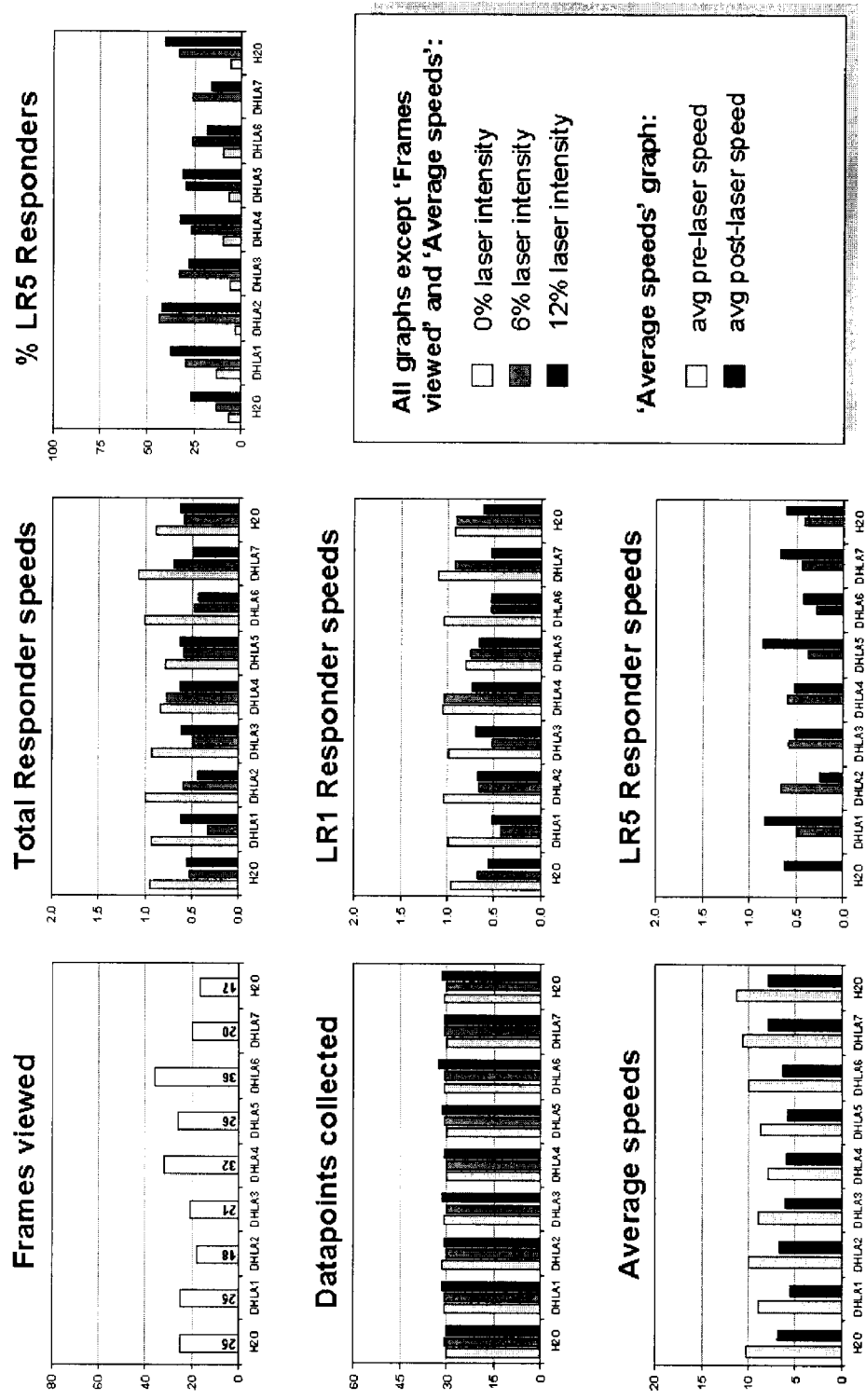
FIG. 5 shows the results of the dose response tests for dihydrolipoic acid described in Example 6.
Figure 6:
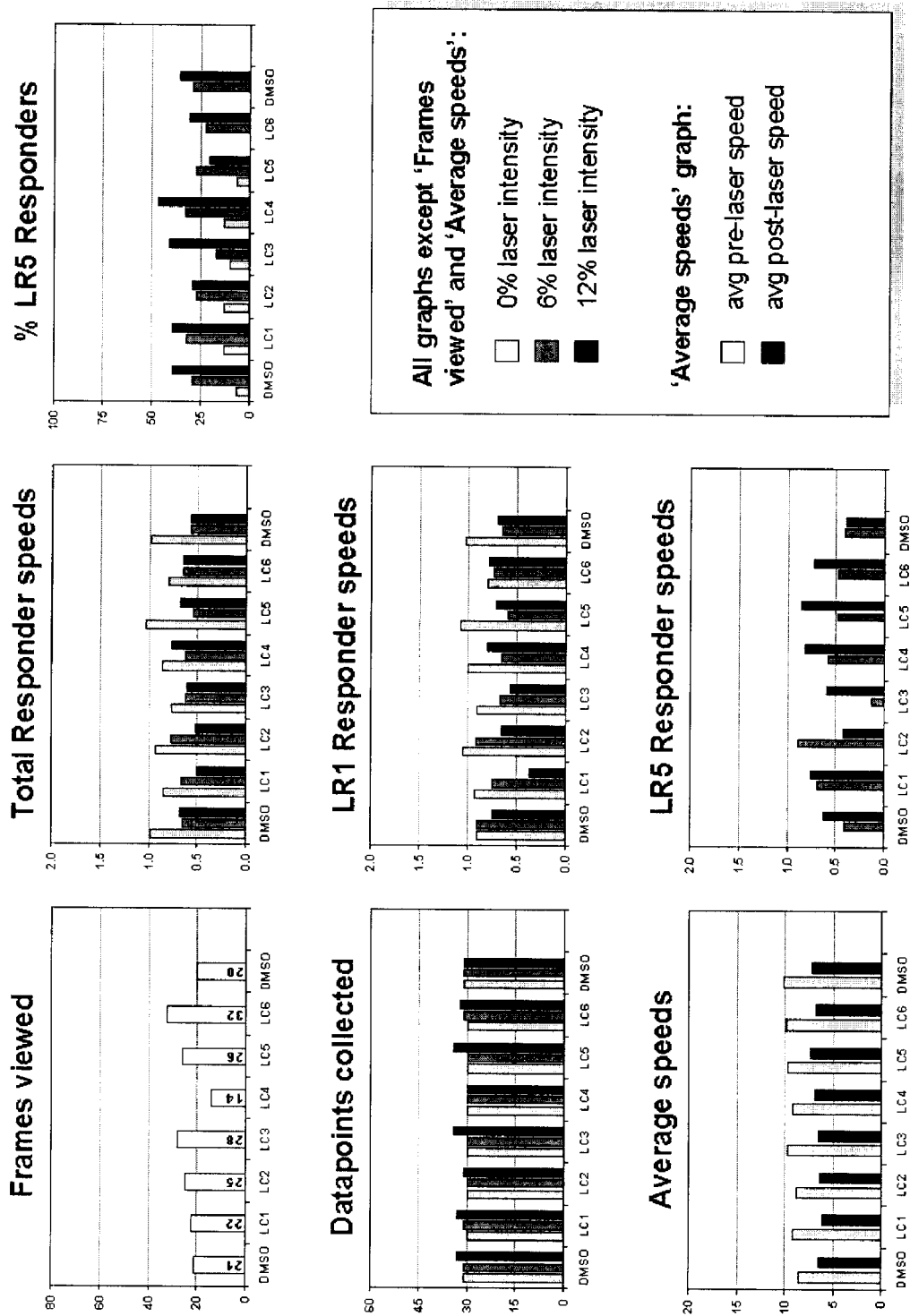
FIG. 6 shows the results of the dose response tests for an LC conjugate described in Example 7.
Figure 7:
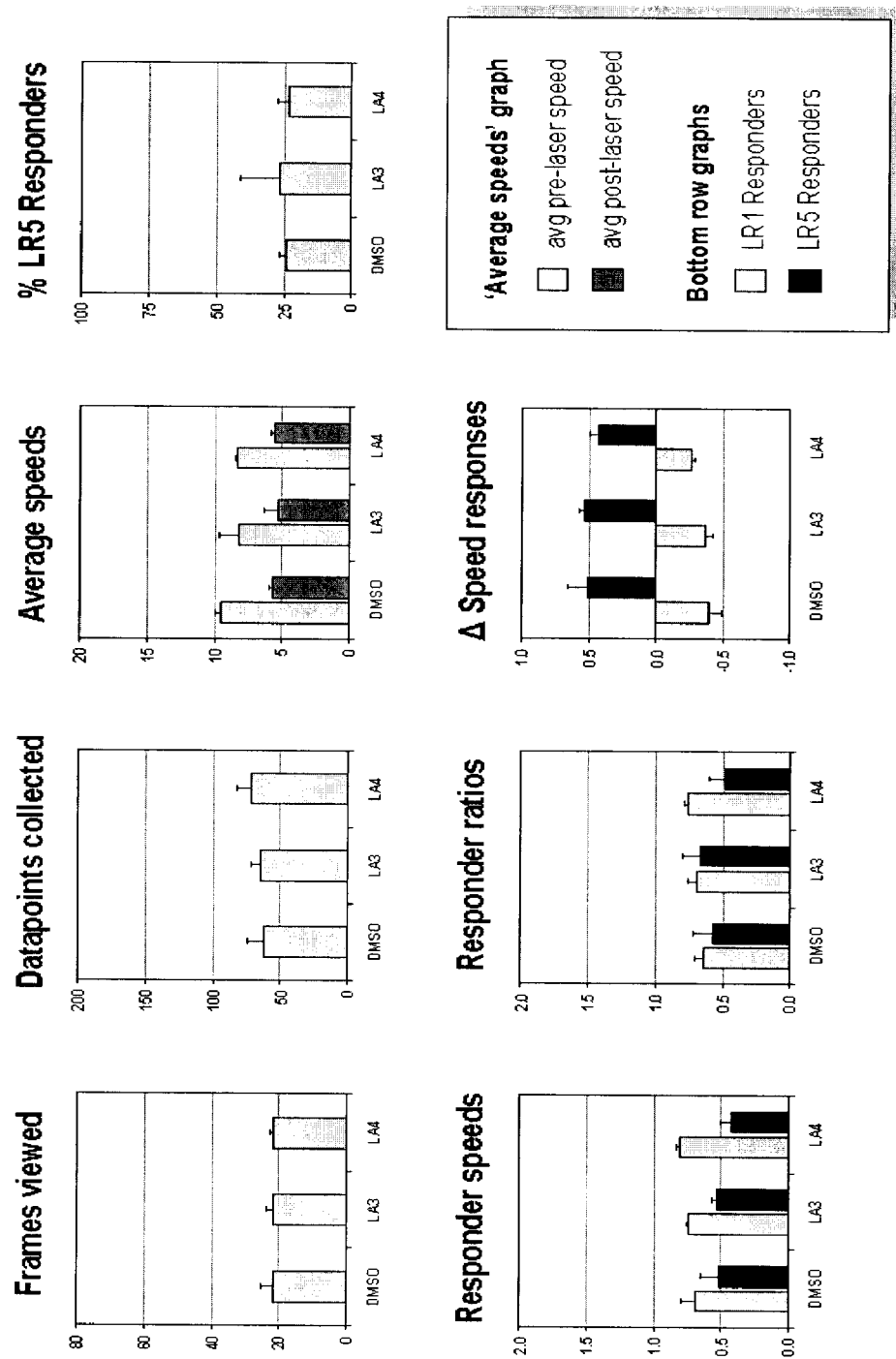
FIG. 7 shows the results of the single intensity tests for lipoic acid described in Example 8.
Figure 8:
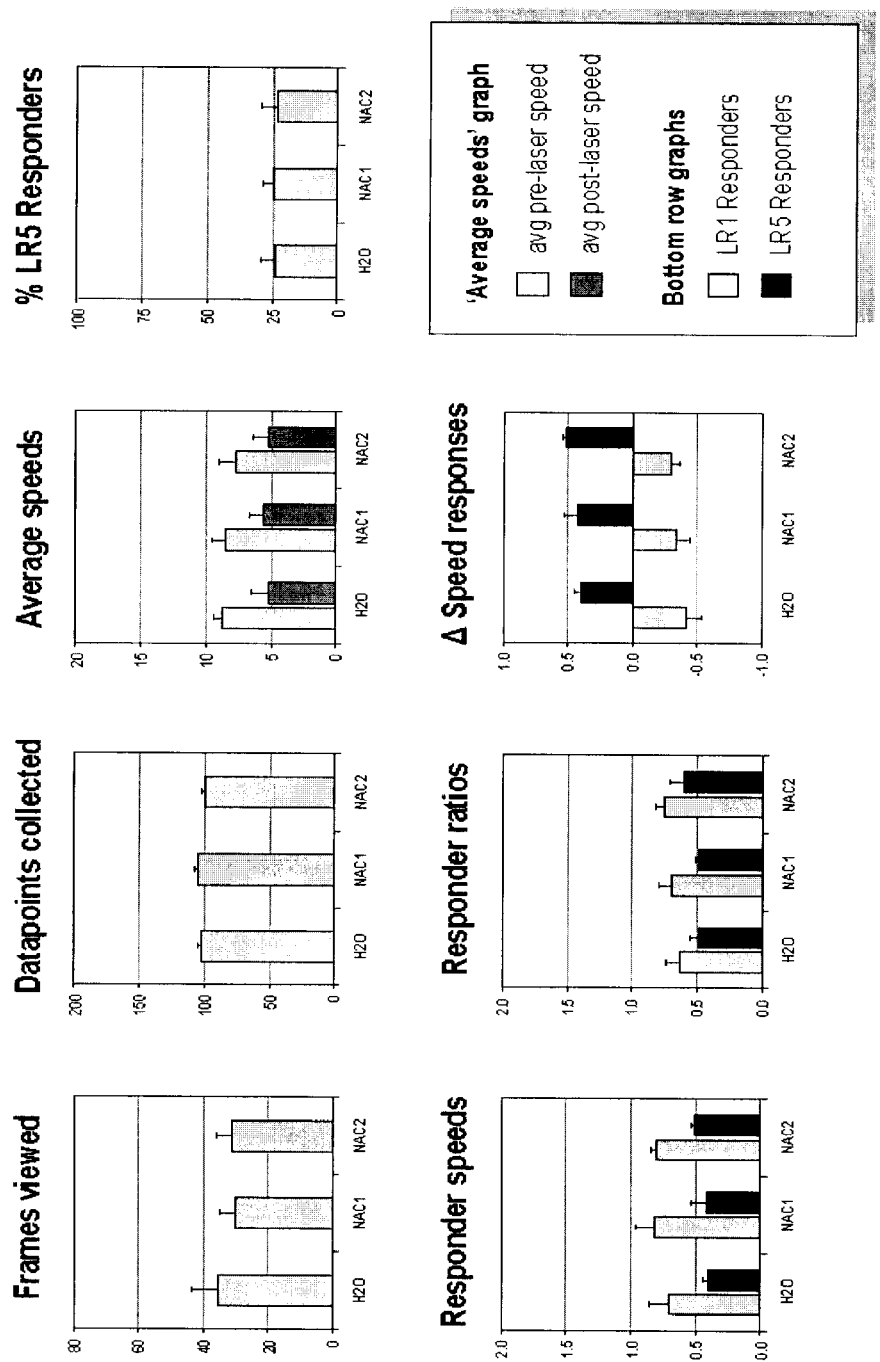
FIG. 8 shows the results of the single intensity tests for carnitine described in Example 8.
Figure 9:
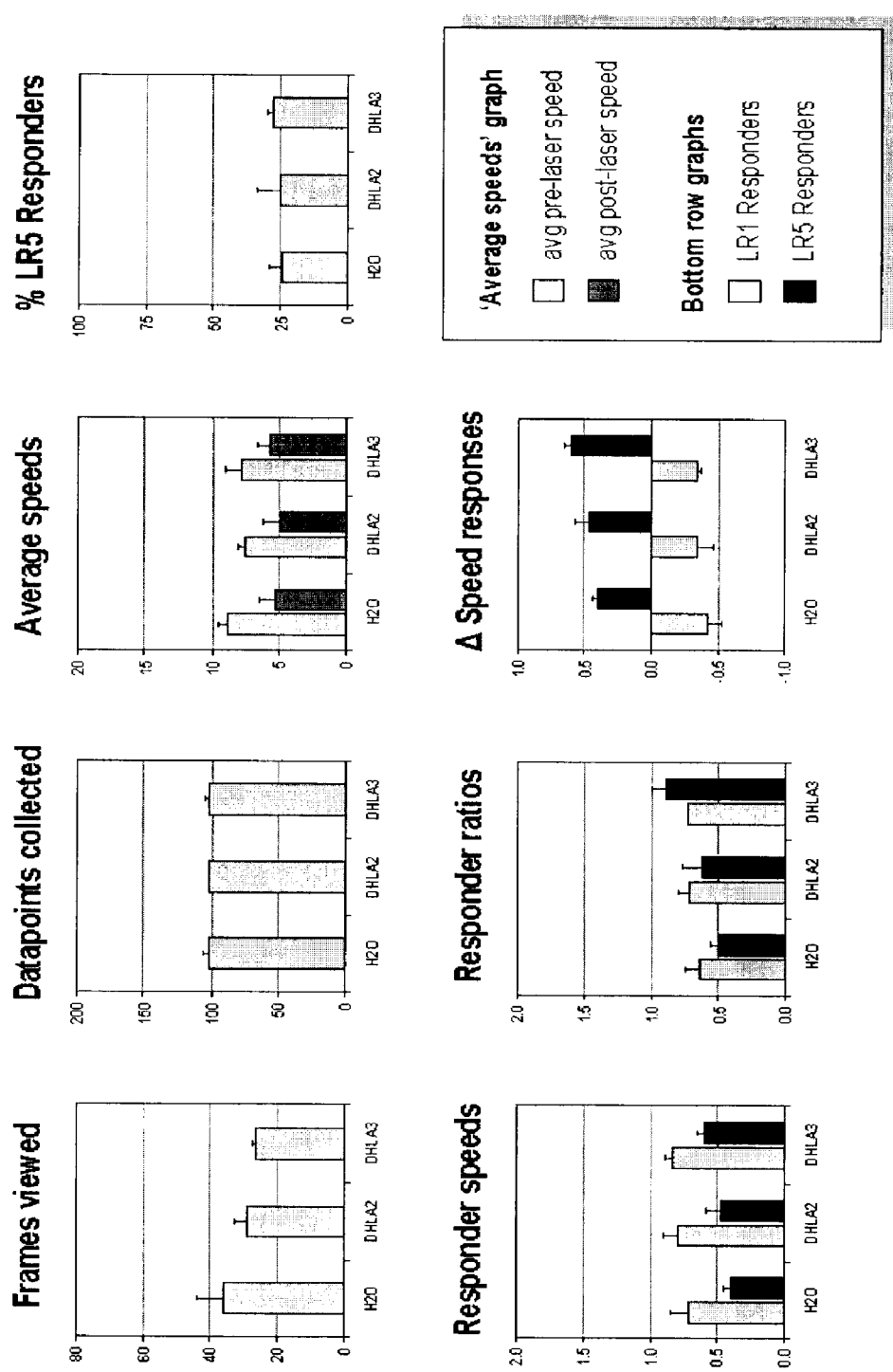
FIG. 9 shows the results of the single intensity tests for dihydrolipoic acid described in Example 8.
Figure 10:
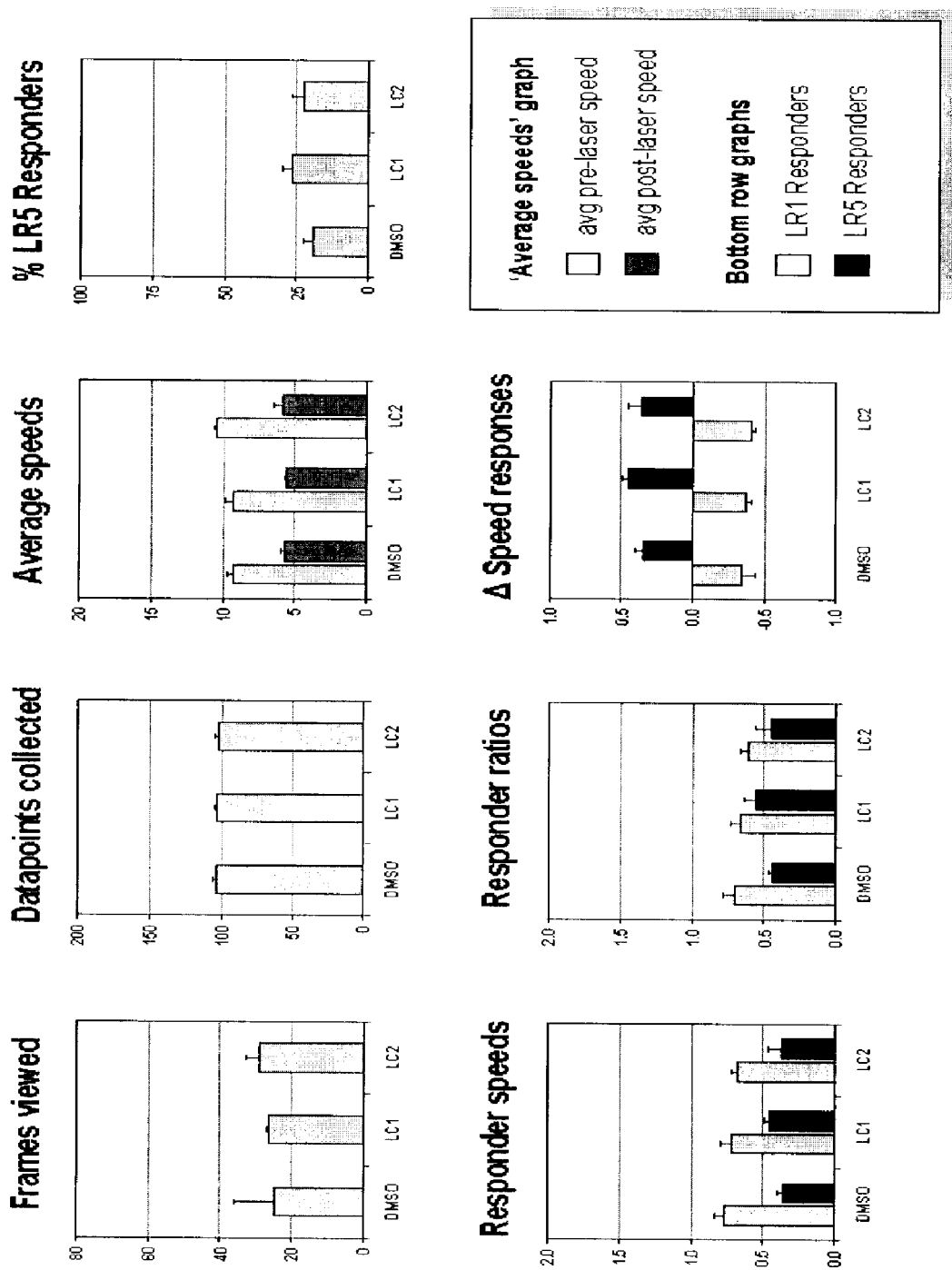
FIG. 10 shows the results of the single intensity tests for the LC conjugate described in Example 9.
Figure 11:
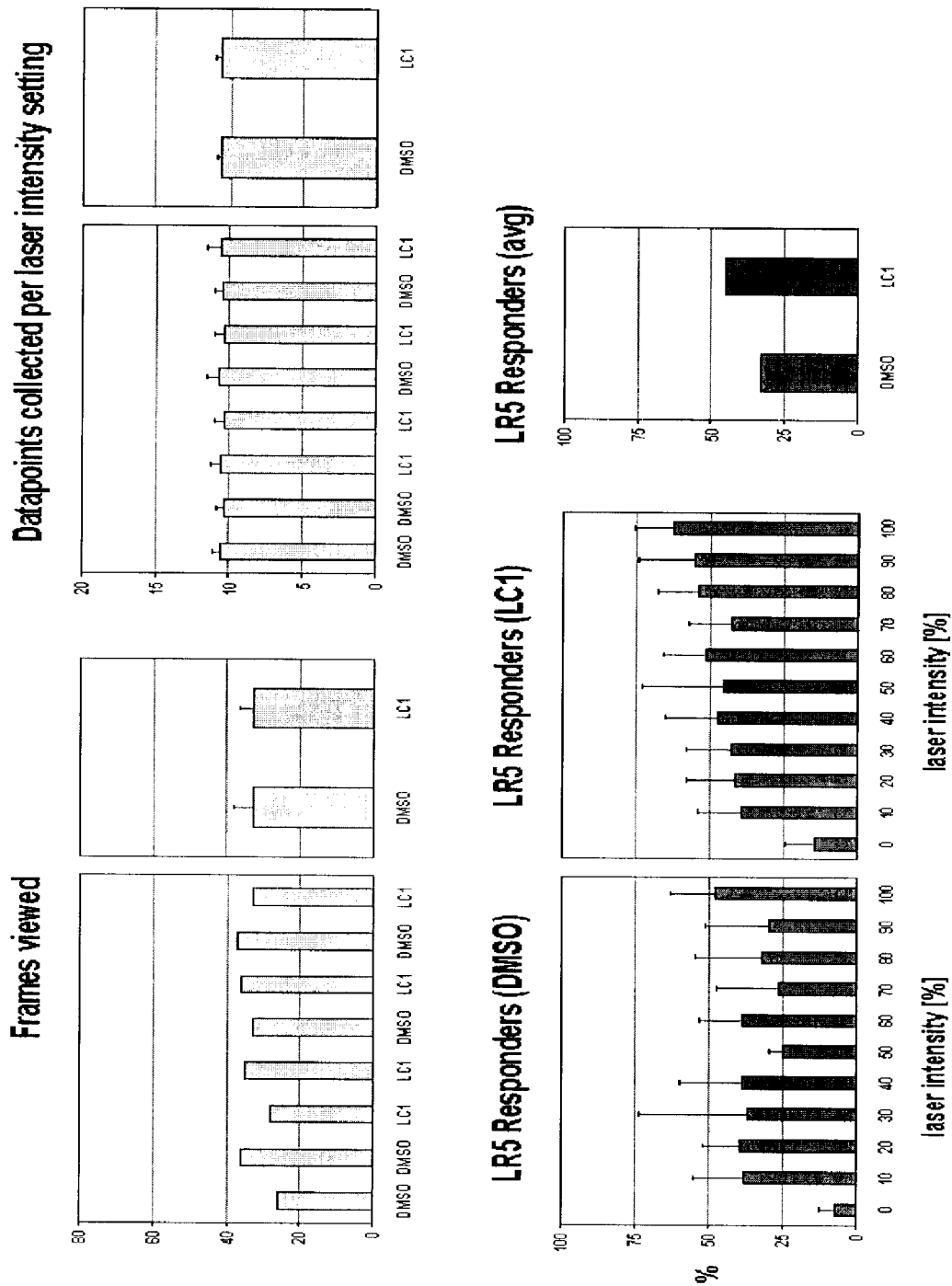
FIG. 11 shows the results of the dose response tests for the LC conjugate described in Example 10.
Figure 12:
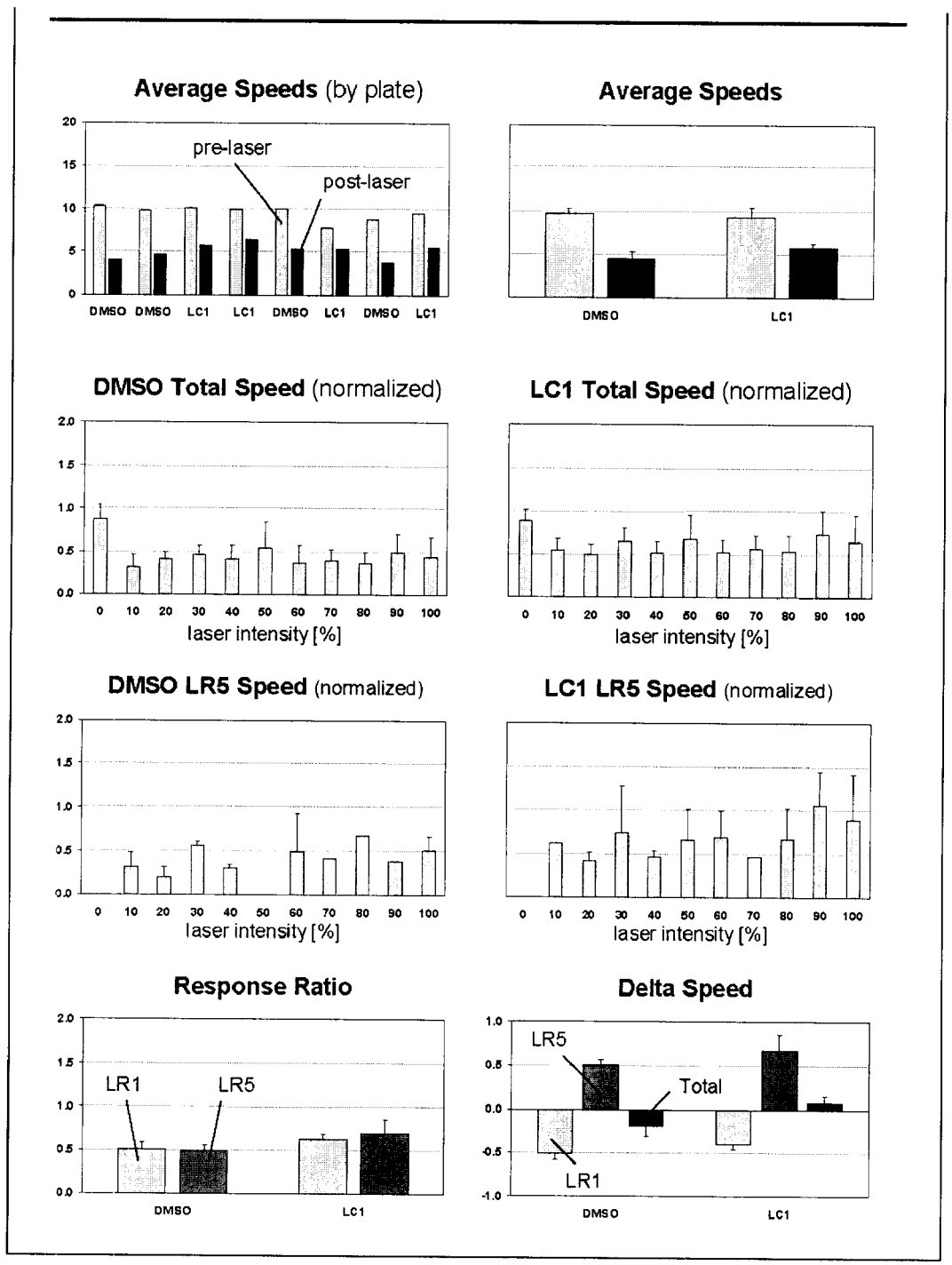
FIG. 12 shows the results of the dose response tests for the LC conjugate described in Example 10.

The present invention provides a novel compound of the general formula A wherein one or more molecules of a carnitine, bound to one or more molecules of a lipoic acid are by a hydrolysable linker to form a single compound. LC conjugate is used herein to refer to any of these compounds of the present invention.

The present invention is also an improved delivery method comprising administering L-carnitine and lipoic acid as a single compound, preferably in which the compound comprises a hydrolysable linkage between the L-carnitine and the lipoic acid.

A carnitine, as used herein, refers to Carnitine is the generic term for a number of compounds that include L-carnitine, L-acetylcarnitine, acetyl-L-carnitine, and L-propionyl carnitine. The only forms available over-the-counter in the US are L-carnitine and acetyl-L-carnitine. L-carnitine is the biological active form. The D-isomer, which is not biologically active, can compete with the L-isomer potentially increasing the risk of L-carnitine deficiency. Proprionyl-L-carnitine is approved for use in Europe but not in the US. Acetyl carnitine is illustrated below as Formula 1.

Lipoic acid, as used herein, refers to 1,2-dithione-3-pentanoic acid, a sulfur-containing anti-oxidant with metal-chelating and anti-glycation capabilities. Unlike many anti-oxidants which are active only in lipid (fat) or aqueous (water) phase, lipoic acid is active in both lipid and aqueous phases. A derivative of lipoic acid is illustrated below as Formula 2.

Lipoic acid and derivatives thereof may be made by substitutions at the molecule's thiol portion. The variants of lipoic acid of the present invention include those in which the carboxylic acid is undisturbed and those in which one or more sulfhydryls are blocked by derivation. In Formula 2, Y is a covalent bond or a pharmaceutically acceptable metal chelate or complex.

Due to an asymmetric carbon having four different attached groups, lipoic acid exists as two enantiomers (mirror images which are chemically unique): the R-enantiomer and the S-enantiomer. Naturally-occurring lipoic acid is the R-form, but synthetic lipoic acid (known as alpha lipoic acid) is a racemic mixture of R-form and S-form. Although the R-enantiomer is more biologically active than the S-enantiomer, administration of alpha lipoic acid actually results in greater formation of DHLA due to a synergistic effect which each enantiomer exerts on the reduction of the other [BIO-FACTORS; Bast, A; 17:207-213 (2003)].

Both LA and DHLA can chelate heavy metals, but the R-form is more effective for chelation than alpha-lipoic acid [BIOCHEMICAL PHARMACOLOGY; Ou, P; 50(1):123-126 (1995)]. LA is most effective in chelating $Cu^{2+}$, $Zn^{2+}$ and $Pb^{2+}$, but cannot chelate $Fe^{3+}$. DHLA forms complexes with $Cu^{2+}$, $Zn^{2+}$, $Pb^{2+}$, $Hg^{2+}$ and $Fe^{3+}$ that are poorly soluble in water. Although DHLA chelates $Fe^{3+}$, it can also reduce $Fe^{3+}$ to $Fe^{2+}$—a pro-oxidant effect it shares with ascorbic acid. Insofar as most iron is tightly bound to ferritin protein, ascorbate reduction of $Fe^{3+}$ rarely occurs, but DHLA may have the capacity to remove bound iron from ferritin.

A linker, as used herein, comprises at least two or more terminal hydroxy groups or a member of Polyethylene Glycol (PEG).

Exemplary linkers are shown in Formulas 4-12 below:

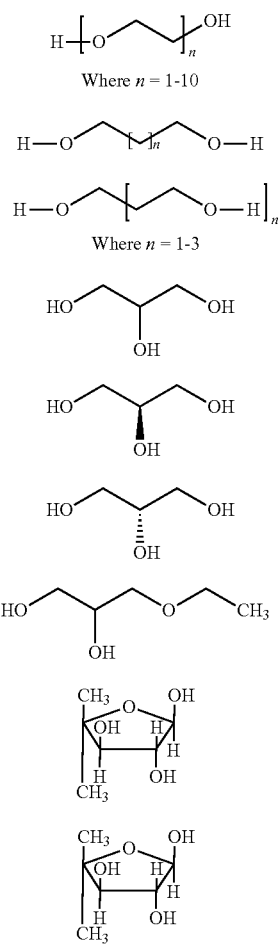

The present invention may also include linkers used in formula A and formula B comprising a molecule of glucose or fructose or appropriately substituted derivatives thereof.

The present invention may also include linkers used in formula A and formula B comprising, but is not limited to any one of formulas 13 to 17, and having any one of:

(i) a phenyl substitutable with any one of chloro, bromo, fluoro, nitro, lower alkoxy or lower alkyl such as methyl ethyl, propyl, isopropyl;

(ii) a butyl substitutable with halogens such as chloro, bromo fluoro; or (iii) a phenyl group substitutable with chloro, bromo fluoro nitro, lower alkyl or alkoxy.

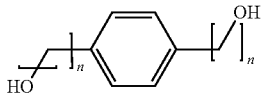

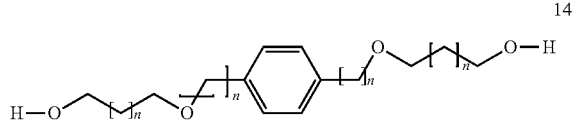

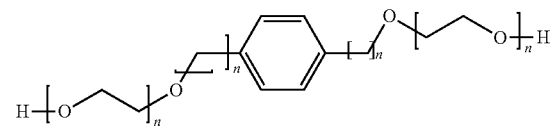

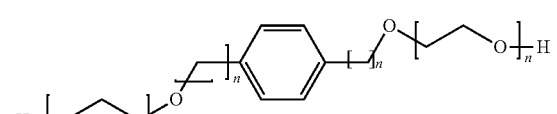

$n = 1-10$

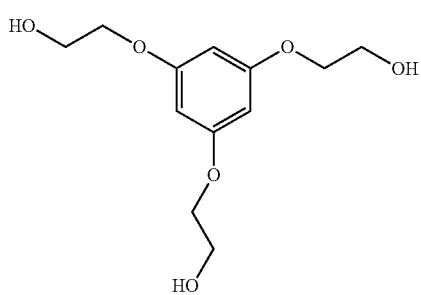

As used herein, hydrolysable intracellularly refers to the chemical or reactive nature of the linker, and is intended to indicate that the linker is substantially stable in all environments except intracellular. Once the compound is positioned or becomes intracellular, it becomes hydrolysable. While not intending to be limited to any particular theory of operation, Applicants' believe the bond is stable at atypical physiological pH (e.g., about 7.4), but is acid cleavable in an acid environment (e.g., at a pH of about less than 6).

As used herein, active site refers to the site in which it is desirable to break or hydrolyze the bond between the carnitine and the lipoic acid derivative. Typically, the active site refers to an intracellular location. Less preferred active sites include those non-intracellular locations in which it may be possible to achieve an acidic environment sufficient to hydrolyze the linkage between the carnitine and the lipoic acid derivative.

The compounds of the present invention provide a more efficient, convenient and precise means of simultaneously delivering formula 1 and formula 2 in controlled relative molar ratios, including but not limited to equimolar ratios.

Formula A, formula 1 and formula 2 are described as follows:

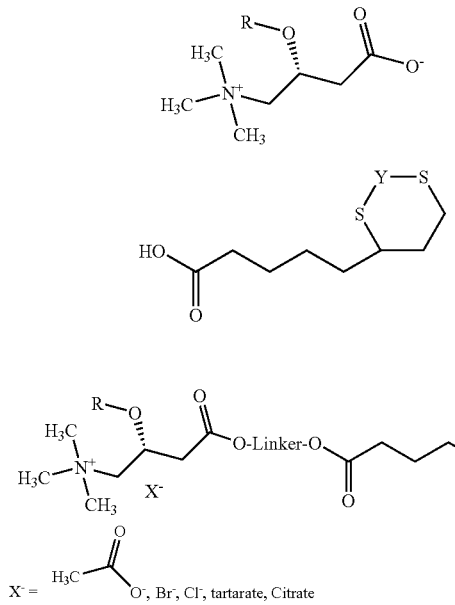

In formula A, R represents hydrogen or $R^1CO—$, wherein $R^1$ is any one of:
(1) a hydrogen;
(2) a phenyl substitutable with chloro, bromo, fluoro, nitro, lower alkoxy or a lower alkyl such as methyl ethyl, propyl, isopropyl;
(3) a butyl substitutable with halogens such as chloro, bromo fluoro;
(4) a phenyl group substitutable with chloro, bromo fluoro nitro, lower alkyl or alkoxy;
(5) a sulfur that can be in sulfoxide or sulfone form; and
(6) a heterocyclic group that can be a five, six or seven member heterocycle with one or two or three or four hetero-atoms such as N, S, SO, $SO_2$ or oxygen.

Y may be a covalent bond or a pharmaceutically acceptable metal chelate or complex.

The present invention also provides a novel compound of the general formula B, wherein one or more molecules of carnitine or a pharmaceutically acceptable salt thereof (e.g., formula 1) is attached to one or more molecules of dihydrolipoic acid or a derivative thereof (e.g., formula 3) in its racemic or pure isomeric form by a hydrolysable linker to form a single compound. This compound provides a more efficient, convenient and precise means of simultaneously delivering formula 1 and formula 3 in controlled relative molar ratios, including but not limited to equimolar ratios.

Formula B, formula 1 and formula 3 are shown as follows:

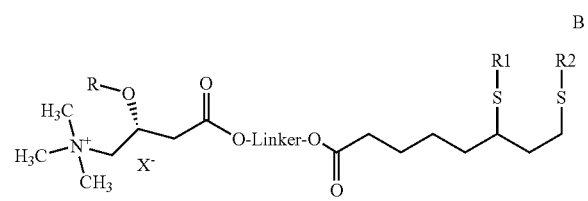

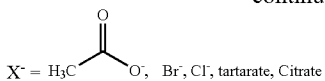

In formula B, R is the same as described above, and $R^2$ and $R^3$ may be each independently hydrogen or $R^4CO—$, wherein $R^4$ comprises:
a. (a) a hydrogen;
b. a phenyl substitutable with chloro, bromo, fluoro, nitro, lower alkoxy or lower alkyl such as methyl ethyl, propyl, isopropyl;
c. a butyl which may be substituted with halogens such as chloro, bromo fluoro;
d. a phenyl group that can be substituted with chloro, bromo fluoro nitro, lower alkyl or alkoxy; or
e. a heterocyclic group that can be a five, six or seven membered heterocycle with one or two or three or four heteroatoms such as N, S, SO, $SO_2$ or oxygen.

Alternatively, in formula B, R2 and R3 may be both or independently $R^4CS—$, wherein $R^4$ is described as above.

Alternatively, in formula B, R2 and R3 may be both or independently one of disulfide alkyl, thiocarbamic ester, and semithioactal.

In accordance with the present invention, compound of Formula A or Formula B comprises a hydrolysable linker that is stable at a pH of about 7.4 and is hydrolysable at a pH of less than about 6.

The compound of formula A provides a more efficient, convenient and precise means of simultaneously delivering formula 1 and formula 2 in controlled relative molar ratios which can be formulated to provide a compound tailored for a given purpose.

The compound of formula B provides a more efficient, convenient and precise means of simultaneously delivering formula 1 and formula 3 in controlled relative molar ratios which can be formulated to provide a compound tailored for a given purpose.

In some embodiments of the invention, a compound comprising formula A or B may be delivered or administered locally, e.g., to a place directly where needed. In these embodiments of the invention, direct or localized delivery may permit effective treatment at a lower concentration.

The present invention also relates to a method of treatment of a mammal, including a human, suffering from a diseases associated with the presence of free radicals in cells, which method comprises administering to said mammal a therapeutically effective amount of a composition comprising a compound selected from the group consisting of formula A or formula B.

Further provided is a method of increasing cellular metabolism while simultaneously alleviating the resultant increase in oxidative stress in a subject, which method comprises administering an effective amount of a composition comprising a compound selected from the group consisting of formula A or formula B.

The present invention provides a novel compound and a better delivery method for improving: cellular metabolism; mitochondria function; mitochondrial membrane stability; lipid transport into mitochondria; acetylcholine biosynthesis; the activity of enzymes producing acetylcholine; protein synthesis; fatty acid metabolism; intracellular ATP levels; neurotophism; sexual sensitivity; mental alertness, memory; cognition; bone density; weight loss; wound healing; blood flow; the condition of the epidermis; motor co-ordination and reaction time; neuromuscular conduction velocity; muscular contraction force; skeletal muscle adaptation to exercise training.

The compound and delivery method provided by the present invention may be useful in preventing or treating:

cardiovascular disease; ischemia; myocardial ischemia; peripheral vascular diseases; arteriosclerosis, damage caused by hypoxia; neuropathies; neurodegenerative diseases; peripheral neuropathies; neuronal lesions; neuronal ischemia; cataracts; age related neurodegeneration; cerebral ischemia; Alzheimer's disease; dementia; cognitive defects associated with substance abuse; anxiety; depression; geriatric depression; cognitive defects associated with aging; noise induced hearing loss; sexual dysfunction; peyronies disease; metabolic diseases; age related metabolic diseases; type II diabetes; protein damage in diabetes; hyperglycemia; accumulation of intracellular sorbitol associated with lesions induced by diabetic; the reduction in insulin-like growth factor associated with aging; or metabolic disorders in glucose utilization L-cartinine deficiencies; genetic defects in L-carnitine biosynthesis; defective intestinal absorption of L-carnitine; defects in lipid metabolism; and obesity; diseases of the epidermis, the effects of aging on the epidermis; alopecia; osteoporosis; bone loss associated with aging; fragile X syndrome: and chronic fatigue syndrome.

One preferred class of compounds to which the present invention relates is described in Formula A, wherein one or more molecules of carnitine, or its appropriate acyl derivative such as acetyl carnitine, (Formula 1) is attached to one or more molecules of lipoic acid or its appropriate derivative (Formula 2) through an appropriate and pharmaceutically acceptable hydrolysable linker of Formula 4 to 12.

In preferred embodiments of the invention formula A and B, the linker is cleavable. In most preferred embodiments, the linker is stable at a pH of 7.4 but acid cleavable at a pH less than 6.

Preferred embodiments of the linker used in the present invention to create molecules of formula A and formula B include but are not limited to a hydrolysable linker:

(a) comprising at least two or more terminal hydroxy groups;
(b) having a formula, including but not limited to any one of formulas 4 to 12;
(c) comprising a member of polyethylene glycol (PEG) group. When a linker belongs to a PEG group, it can be of varying complexity and of varying molecular weight up to 500,000 (units);
(d) comprising a molecule of any one of glucose, fructose or appropriately substituted derivatives thereof;
(e) comprising, but is not limited to any one of formulas 13 to 17, and having any one of:
  (i) a phenyl substitutable with any one of chloro, bromo, fluoro, nitro, lower alkoxy or lower alkyl such as methyl ethyl, propyl, isopropyl;
  (ii) a butyl which substitutable with halogens such as chloro, bromo fluoro; or
  (iii) a phenyl group substitutable with chloro, bromo fluoro nitro, lower alkyl or alkoxy.

The preferred lipoic acid and dihydrolipoic acid derivatives used respectively in Formula A and Formula B will vary according to the cell type and/or disease to be targeted for treatment.

The compositions of the present invention may be delivered or administered by any pharmaceutically acceptable route.

The compound of the present invention may be administered orally as a dietary supplement in solid, semi-solid or liquid form.

The compound of the present invention can be adapted for delivery orally, parenterally, rectally, or transdermally in the form of a medicament.

The compound can be adapted for topical delivery in solid, semi-solid or liquid form as a medicament.

In certain embodiments of the present invention, the compound can be administered locally at the site where its activity is needed and therefore at lower concentrations than would be required for systemic delivery.

Having regard to the specific route of administration, convenient unit dosage containers and/or formulations include tablets, capsules, lozenges, troches, hard candies, powders, metered sprays, creams, lotions, ointments suppositories, patches or liquid preparations such as oral or sterile parenteral solutions or suspensions, etc.

Those skilled in the art will understand that that the mode of administering the compounds of the claimed invention may depend on the disease, condition, and/or symptom being treated.

The compound may be delivered in combination with a pharmaceutically acceptable, carrier, excipient and/or other pharmaceutically active agent(s) having regard to the specific route of administration. For example, the compound may be used in combination with other therapeutic or prophylactic agents. For example, the compound may be used in conjunction with other antioxidants, free radical scavengers, etc., and mixtures thereof, see e.g. Goodman & Gilman's The Pharmacological Basis of Therapeutics, 9th Ed., 1996, McGraw-Hill. Appropriate excipients to be used to prepare the compositions employing this compound will be known to those skilled in the art.

Methods for making and preparing carnitine and active carnitine derivatives are known in the art, e.g. U.S. Pat. Nos. 4,766,222 (Novel class of acyl-derivatives of carnitine process for preparing same and therapeutic use thereof); 4,673,534 (Carnitine salts particularly suitable for oral use); 4,743,621 (Ester of acetyl carnitine, processes for its preparation and pharmaceutical compositions containing it); 4,593,043 (Mercapto acyl-carnitines and pharmaceutical compositions containing same); 4,590,209 (Alkoxy-acyl carnitines and pharmaceutical compositions containing same); 4,567,200 (Esters of mercapto acyl-carnitines and pharmaceutical compositions containing same); 4,032,641 (Nicotinoyl carnitine derivatives); 4,551,477 (Esters of alkoxy-acylderivatives of carnitine and pharmaceutical compositions containing same); 4,401,827 (Novel acyl-derivatives of carnitine and process for their preparation); 5,260,464 (Carnitine derivatives, process for their preparation, and their use in human therapy); 4,859,698 (Novel class of acyl-derivatives of carnitine, process for preparing same and therapeutic use thereof); 4,692,543 (Optically-activedi-[3-chloro-2-oxy-propyltrimethylammonium]-tartrate); 5,258,552 (N-alkylamides of d(+)-carnitine having antibacterial activity, process for their preparation and pharmaceutical and cosmetic compositions containing same); etc.

The methods of formulation, synthesis and production of the mitochondrially active lipoic acids are known. For example, lipoic acid derivatives and their methods of production are well described, e.g. U.S. Pat. Nos. 5,621,117 (Method for the racemization of enantiomers of .alpha.-lipoic acid); 5,489,694 (Preparation of R/S-gamma-lipoic acid or R/S-alpha-lipoic acid); 5,463,093 (Palladium complexes and methods for using same in the treatment of tumors or Psoriasis); 5,334,612 (Pharmaceutical compositions containing as active substance sulphur-containing carboxylic acids and their use in combating retroviruses); 4,390,620 (Method and composition for the detection and study of cellular activity or the like and means for applying such method); 5,118,505 (Combination preparation for the treatment of nerve cell and nerve fibre diseases and injury); 4,767,704 (Protein-free culture medium).

Bioactivity assays are described in WO98/576227 or in the references cited herein. For example, cardiolipin content is readily assayed as referenced in Guan, Z. Z., Soderberg, M., Sindelar, P., and Edlund, C. Content and Fatty Acid Composition of Cardiolip in the Brain of Patients with Alzheimer's Disease. Neurochem. Int. 25: 295-300, 1994 and oxidant production (DCFH) may be assayed as described by LeBel, C. P., Ischiropoulos, H., and Bondy, S. C. Evaluation of the Probe2',7'-Dichlorofluorescin as an Indicator of Reactive Oxygen Species Formation and Oxidative Stress. Chem. Res. Toxicol. 5: 227-231, 1992.

The present invention provides administratively convenient formulations of α-L-lipoic acid and acetyl-L-carnitine compound. Dosages of the acetyl-L-carnitine and α-L-lipoic acid for administered by oral means, amount to a daily dose of 1000 mg of acetyl-L-carnitine and about 400 mg of α-L-lipoic acid, although variations will necessarily occur depending on the formulation, host, body weight etc.

EXAMPLES

Example 1 washed with acetone. Residue was then dried under vacuum to provide intermediate 3 as a dark oil.

Acetyl-L-Carnitine-Lipoic acid conjugate (4)

To a solution of crude intermediate-3 obtained from previous experiment in dry acetonitrile (15 ml) was added DMAP (1.25 mmol), alpha-Lipoic acid (1.25 mmol) and DCC (1.25 mmol) at room temperature and the resultant reaction mixture was stirred for 18 hrs. Separated urea was removed by filtration and the filtrate was washed with saturated sodium bicarbonate solution. Organic layer was separated and concentrated to obtain LC Conjugate in crude form. Pure LC Conjugate 4 was isolated by column chromatography using silica gel. NMR (DMSO $d_6$) δ: 5.45 (m, 1H), 4.2-4.4 (m, 2H), 4.05 (m, 2H), 3.7-3.9 (m, 2H), 3.50-3.65 (m, 2H), 3.12 (m, 9H), 2.75 (m, 2H), 2.50 (m, 2H), 2.07 (s, 1H), 2.05 (m, 3H), 1.20-1.98 (m, 8H) ppm.

Example 2

Hydrolysis Study of LC Conjugate

A pH/Time Study
Preparations:
Control: Free lipoic acid 1% solution in methanol/water
Substrate: LC Conjugate, 3% solution in methanol
Experiment:
  A study on the stability and cleavability of LC Conjugate was performed in water at pH ranged from 5.5 to 8.0 at RT (20° C.).

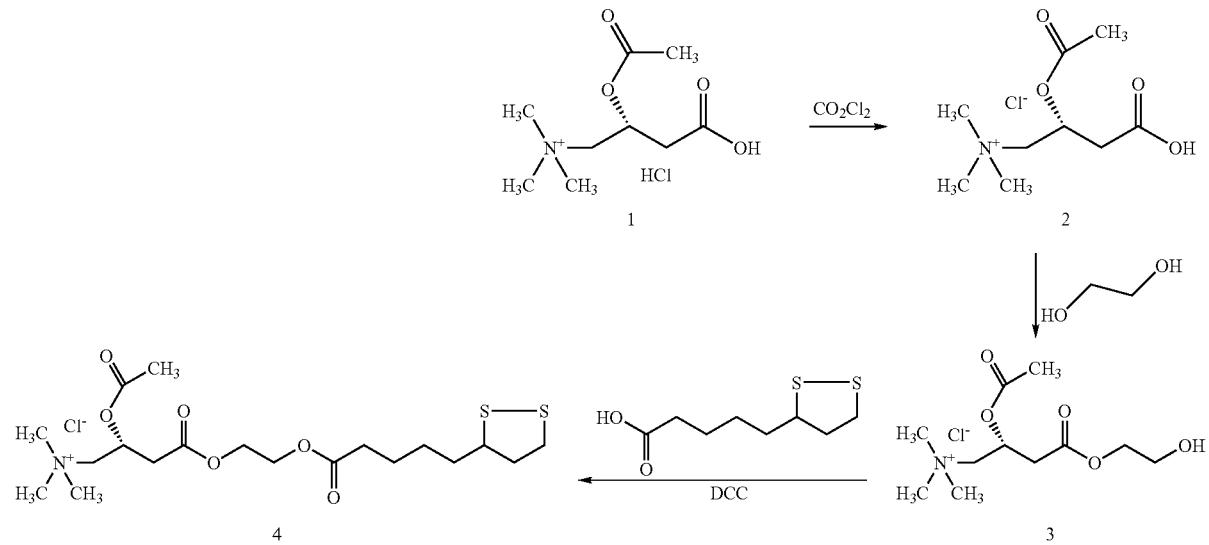

Scheme

Acetyl-L-Carnitine hydroxylethyl ester (3)

To a suspension of Acetyl-L-carnitine (1.25 mmol) in 5 ml dichloromethane was added oxalyl chloride (2.2 mmol) at room temperature for four hours. To the resultant reaction mixture ethylene glycol (5 mmol) was added at room temperature and the reaction mixture was stirred overnight. Separated solid was removed by filtration and then washed with acetone. Filtrate and acetone washings were combined and evaporated to an oily residue, which was then repeatedly The pH was adjusted using NaOH and HCl solutions.
Since substrate and cleaved products are non-UV sensitive, TLC was used to follow the progress of hydrolysis.
The following results were obtained based on visual observations:
  1. LC Conjugate seems to be stable under pH 5.0
  2. Mild hydrolysis was noted at pH 6.0
  3. At pH 7.0 and above rate is quite noticeable
  4. At pH 8.0 almost complete hydrolysis was noted within 90 minutes Conclusion:
1. Rate of hydrolysis (cleavage) is pH dependent.
2. LC Conjugate is completely cleavable under experimental conditions.

Example 3

The soil nematode *C. elegans* is arguably the best characterized animal in modern biology. *C. elegans* is well suited for nervous system studies as the complete set of 302 neurons are anatomically simple, thoroughly characterized and known to utilize the same neurotransmitters found in vertebrates. Other molecular functions and signaling pathways, including key receptors and ion channels, are conserved between *C. elegans* and vertebrates. Importantly, pharmacologic features are also generally conserved (for example, just as in humans, the activity of the *C. elegans* serotonin reuptake transporter is modulated by Prozac) and suitable behavioral read-outs allow quantification of genetically, or drug-induced alterations of neurological function. As such, *C. elegans* can be a useful model to identify and quantitate the effects of pharmaceutically active compounds with potential therapeutic benefits in human neurological indications.

The present invention includes a series of compounds that may be useful for increasing sensory neuron function in certain human neuropathological conditions. *C. elegans* contains a number of sensory neurons which are responsible for detecting a variety of external stimuli. One such stimulus (heat) can be detected and quantified in *C. elegans* by the use of thermal avoidance (TAV) technology available through NemaRx. The goal of this experiment was to provide an initial characterization of the compounds via TAV. Specifically, it was asked whether any of these compounds can lead to an increase in the thermal stimulus-induced behavioral response measured by TAV. N2 strain *C. elegans* animals were used for this project, which have 'normal', i.e. wildtype, sensory neuron function. Four compounds were received by NemaRx for TAV testing. These compounds were:
LC Conjugate; Lipoic Acid+N-Acetyl carnitine conjugate
DHLA: Dihydrolipoic acid
LA: Lipoic acid
NAC: N-Acetyl carnitine HCl The work plan included a i) characterization of the compounds for toxicity in *C. elegans* and then, using subtoxic concentrations, a ii) characterization of compound effects on neuronal sensitivity as detected by TAV technology. Toxicity characterization follows a well established standard operating protocol used in previous toxicity-type assays in *C. elegans*. The initial TAV characterization of compound-mediated effects on *C. elegans* used a number of compound concentrations and incubation times that were selected by NemaRx as being most likely to detect any TAV-related effects that the compounds may have. A summary of the results follows:

Toxicity: No toxic effects were observed for NAC or LC even at the highest concentrations tested, 8 mM and 2 mM respectively. LA showed intermediate toxicity at the highest concentration (10 mM) and weak toxicity at 5 mM. DHLA showed weak toxicity at the highest concentration tested (1:500 dilution).

3 Step Dose Responses: All compounds (and dilutions) were initially tested for effects on the TAV response at stimulus-intensities of 0%, 6% and 12% max laser intensity. 0% provides a 'background' measure, 6% typically gives intermediate TAV responses (and as such should provide a good starting point to detect compound-mediated increased TAV responses), and 12% usually gives robust responses. No obvious effects were detected for either of the four compounds. While the experimental setup provides a good first pass, the limitation lies in the relatively small number of animals that are assayed at each intensity (30). Subtle effects compound-mediated up-regulation at 6% laser intensity may be missed.

Single Intensity Testing: The two highest non-toxic compound concentrations for each of the four compounds were tested at 6% laser intensity. The number of datapoints collected was between 50-80 LA and >100 for the three other compounds. No obvious effect was noted with either of the compounds.

11 Step Dose Responses: The highest concentration of LC was tested in a dose response experiment with laser intensities ranging from 0% to 100% in 10% intervals. The experiment was carried out in quadruplicate. The results may suggest that LC increases sensitivity not at lower stimulus intensities, but instead at higher intensities. A variety of interpretations of this result are possible (for example: LC may help to overcome desensitization issues resulting from repeated stimulation of the sensory neuron). Additional follow-up studies should be done to confirm this result.

Stock Dilution Setup

Compounds received April 21 in cooler (with ice)

Plastic container with the vials was removed and placed at −80 C

Stocks
1. Lipoic acid (CAS 1077-28-7; MW 206.3): 8 mg dissolved in 39 µl DMSO for 1 M stock
2. Dihydrolipoic acid (CAS 7516-48-5; MW 208.3): 5 µl diluted in 45 µl dH$_2$0 for 1:10 dilution
3. N-Acetyl carnitine (CAS 5080-50-2; MW 239.70): 10 mg diluted in 104 µl dH$_2$0 for 0.4M stock
4. NOU-0604-022 (MW 474.1): resuspended in 401 µl DMSO for 0.2M stock Dilutions
1. Lipoic acid (LA)

| | dilution | | | | | | |
|---|---|---|---|---|---|---|---|
| Stock | 1000 mM | 500 mM | 200 mM | 100 MM | 50 mM | 10 mM | 1 mM |
| µL DMSO | 39 | 15 | 15 | 10 | 10 | 40 | 90 |
| µL from higher dilution | — | 15 | 10 | 10 | 10 | 10 | 10 |
| mg compound | 8 | — | — | — | — | — | — |
| abbreviation | LA1 | LA2 | LA3 | LA4 | LA5 | LA6 | LA7 |

2. Dihydrolipoic acid (DHLA):

| | | | | dilution | | | |
|---|---|---|---|---|---|---|---|
| Stock | 1:10 | 1:20 | 1:50 | 1:100 | 1:1000 | 1:10000 | 1:100000 |
| μl DSMO | 45 | 20 | 30 | 20 | 90 | 90 | 90 |
| μl from higher dilution | — | 20 | 20 | 20 | 10 | 10 | 10 |
| mg compound | 5 | — | — | — | — | — | — |
| abbreviation | DHLA1 | DHLA2 | DHLA3 | DHLA4 | DHLA5 | DHLA6 | LDHA7 |

3. N-Acetyl carnitine (NAC)

| | | | dilution | | | |
|---|---|---|---|---|---|---|
| Stock | 400 mM | 200 mM | 100 MM | 50 mM | 10 mM | 1 mM |
| μl dH20 | 104 | 25 | 25 | 25 | 80 | 90 |
| μl from higher dilution | — | 25 | 25 | 25 | 20 | 10 |
| mg compound | 10 | — | — | — | — | — |
| abbreviation | NAC1 | NAC2 | NAC3 | NAC4 | NAC5 | NAC6 |

4. Lipoic acid/Carnitine conjugate (LC):

| | | | dilution | | | |
|---|---|---|---|---|---|---|
| Stock | 200 mM | 100 MM | 50 mM | 10 MM | 1 MM | 0A MM |
| μl DMSO | 401 | 100 | 100 | 160 | 180 | 180 |
| μl from higher dilution | — | 100 | 100 | 40 | 20 | 20 |
| mg compound | 38 | — | — | — | — | — |
| abbreviation | LC1 | LC2 | LC3 | LC4 | LC5 | LC6 |

Stocks and dilutions were frozen at −80 C and kept in the dark when not in use.

Example 4

Toxicity Testing—NAC, LA, & DHLA

Two 96 well microtiter plates set up which were incubated at 20 C (both 96 well plates were identical, i.e. the experiment was done in duplicate). Each well on the plates was set up with 100 L1-stage N2 animals in NGM with a 1:20 dilution of concentrated HB101 *E. coli* (food source) in a volume of 50 μl. Compounds (see below) were then added to the wells. For water controls and compound stocks/dilutions in water (DH LA, NAC) 1 μl was added to each well (1:50 dilutions). For DMSO controls and compound stocks/dilutions in DMSO (LA) 0.5 μl was added to each well (1:100 dilutions). OD620 measurements were taken immediately after plate setup, after 20 hours and 44 hours (the assay relies on 'bacterial clearance', whereby growing animals feed on *E. coli*, thus reducing the amount of bacteria in the well over time; OD620 values of 0.05-0.07 indicate that all bacteria have been consumed and that the animals have grown to a late larval/early adulthood stage).

Compound distribution on 96 well plates for tox test:

| | 1 | 2 | 3 | 4 | 5 | 6 | 7 | 8 | 9 | 10 | 11 | 12 |
|---|---|---|---|---|---|---|---|---|---|---|---|---|
| A | H2O | H2O | H2O | DMSO | DMSO | DMSO | LA7 | LA7 | LA7 | | | |
| B | NAC1 | NAC1 | NAC1 | DMSO | DMSO | DMSO | DHLA1 | DHLA1 | DHLA1 | | | |
| C | NAC2 | NAC2 | NAC2 | LA1 | LA1 | LA1 | DHLA2 | DHLA2 | DHLA2 | | | |
| D | NAC3 | NAC3 | NAC3 | LA2 | LA2 | LA2 | DHLA3 | DHLA3 | DHLA3 | | | |
| E | NAC4 | NAC4 | NAC4 | LA3 | LA3 | LA3 | DHLA4 | DHLA4 | DHLA4 | | | |
| F | NAC5 | NAC5 | NAC5 | LA4 | LA4 | LA4 | DHLA5 | DHLA5 | DHLA5 | | | |
| G | NAC6 | NAC6 | NAC6 | LA5 | LA5 | LA5 | DHLA6 | DHLA6 | DHLA6 | | | |
| H | H2O | H2O | H2O | LA6 | LA6 | LA6 | DHLA7 | DHLA7 | DHLA7 | | | |

Conclusions:
N-Acetyl carnitine: no toxicity observed even at highest concentration (8 mM)
Lipoic Acid: toxicity observed at highest (10 mM) and second-highest concentration (5 mM)
Diydroolipoic acid: no obvious toxicity observed (possible subtle effect at highest concentration of 1:500 final—additional test should be performed to confirm)

Example 5

Toxicity Testing—LC

One 96 well microtiter plate set up and incubated at 20 C (experiment done in duplicate on same plate). Each well on the plates was set up with 100 L1-stage N2 animals in NGM with a 1:20 dilution of concentrated HB101 *E. coli* (food source) in a volume of 50 μl. Compounds (see below) were then added to the wells. For the DMSO controls and LC stocks/dilutions in DMSO 0.5 μl was added to each well (1:100 dilutions). OD620 measurements were taken immediately after plate setup, after 21 hours and 44 hours.

Compound distribution on 96 well plate for tox test:

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   | DMSO | LC1 | LC2 | LC3 | LC4 | LC5 | LC6 | DMSO |
| B |   |   |   |   | DMSO | LC1 | LC2 | LC3 | LC4 | LC5 | LC6 | DMSO |
| C |   |   |   |   | DMSO | LC1 | LC2 | LC3 | LC4 | LC5 | LC6 | DMSO |
| D |   |   |   |   | DMSO | LC1 | LC2 | LC3 | LC4 | LC5 | LC6 | DMSO |
| E |   |   |   |   | DMSO | LC1 | LC2 | LC3 | LC4 | LC5 | LC6 |   |
| F |   |   |   |   | DMSO | LC1 | LC2 | LC3 | LC4 | LC5 | LC6 |   |
| G |   |   |   |   |   |   |   |   |   |    |    |   |
| H |   |   |   |   |   |   |   |   |   |    |    |   |

Experiment 1: A5-C5, A6-C6, A7-C7, A8-C8, A9-C9, A10-C10, A11-C11, A12-C12
Experiment 2: D5-F5, D6-F6, D7-F7, D8-F8, D9-F9, D10-F10, D11-F11, D12-F12
Conclusions:
  LC: no toxicity observed even at highest concentrations (2 mM)

Example 6

Dose Response Testing (3step)—NAC, LA & DHLA

One 24 well microtiter plate was set up and incubated overnight on the shaker at 20 C. Each well on the plate was set up with 600 L3/L4-stage N2 animals in NGM with a 1:20 dilution of concentrated HB101 *E. coli* (food source) in a volume of 300 µl. Before the animal/HB101 solution was added, test compounds were pipetted into wells. For water controls and compound stocks/dilutions in water (DHLA, NAC) 6 µl was added to each well (1:50 dilutions). For DMSO controls and compound stocks/dilutions in DMSO (LA) 3 µl was added to each well (1:100 dilutions). No OD620 measurements were taken but the animals were visually scored after 19 h incubation.

Compound distribution on 24 well plate for TAV test:

|   | 1 | 2 | 3 | 4 | 5 | 6 |
|---|---|---|---|---|---|---|
| A | H2O | NAC4 | DHLA2 | DHLA6 | LA1 | LA5 |
| B | NAC1 | NAC5 | DHLA3 | DHLA7 | LA2O | LA6 |
| C | NAC2 | NAC6 | DHLA4 | H2O | LA3 | LA7 |
| D | NAC3 | DHLA1 | DHLA5 | DSMO | LA4 | DSMO |

Visual scoring after 19 h incubation: Most wells had cleared (HB101 bacteria removed by growing N2 animals) and most animals had reached adulthood stage with some eggs in wells, but yet only very few or no L1 progeny animals. Wells that had not completely cleared were:
  D2: DHLA1 (1:500 final concentration in well) some bacteria remaining; in general animals appear a bit smaller and less mobile than in other completely cleared wells
  A5: LA1 (10 mM final concentration in well) most bacteria remaining; animals do not appear to have grown much from the initial L3/L4

| Data Collection | | Data analysis | |
|---|---|---|---|
| Laser intensity mode: | :dose response | min speed limit: | 0.0 |
| No. steps | 3 | max speed limit: | 40.0 |
| (laser intensities): | (0%, 6%, & 12%) | average speed | omitted if <5 |

-continued

| Data Collection | | Data analysis | |
|---|---|---|---|
| Step size: | 6% | calculation: | datapoints |
| Min no. data collect/step: | 30 | | |
| Time collection limit: | 10 minutes | | |
| XY scan mode: | scanline | | |
| Min frame threshold: | 1 | | |
| Max frame threshold: | 500 | | |
| Firing rounds/frame | 2 | | |
| Min movement ratio: | 2.5 | | |
| Max movement ratio: | no limit | | | stage and about have of the animals show a 'stiff rod' phenotype, i.e. are most likely dead
  B5: LA2 (5 mM final concentration in well) some bacteria remaining; on average animals appear a bit smaller than in other completely cleared wells (for example LA3)
Dose Responses—setup: All of the wells from the 24 well plate were used for dose response testing and the entire well contents (600 animals) were used for each test. Prior to being placed on the agar plate for TAV testing each sample was processed as follows:
  sample were transferred to glass tube containing 7 ml PBS
  animals were allowed to settle for 5 minutes before most of the supernatant was removed (approx. 0.5 ml remaining in tube)
  7 ml PBS was then added, mixed and animals were allowed to settle for 5 minutes most of the supernatant was then removed
  animals were removed and transferred to TAV testing plate (NRx Application pattern A)
  plate was allowed to dry for 10 minutes (plate cover removed) and TAV testing was initiated.
Per plate settings for the dose response experiments were as follows:
  Dose Responses—general notes on analysis: A response of the animals to a thermal stimulus (laser) which is applied to the head region can be detected both by a change in the direction of movement, as well as by a change in speed occurring within the test interval where the stimulus is applied.
    direction of movement. Animals that do not change the direction of movement (within certain limits) in response to the laser are classified as LR1 responders. Animals that show a strong change in the direction of movement, i.e. reversals, are classified as LR5 responders. Intermediate changes in the direction of movement (LR2, LR3 & LR4) usually account for less than 10% of the observed responses and are not relevant for the current project
    speed: Animals that do not show a change in movement direction, i.e. LR1 responders, show a thermal intensity-dependent reduction in the speed of forward movement. LR5 responders show a thermal intensity-dependent increase in the speed of movement (starting off with less than <prelaser speed at low intensities up to > pre-laser speed at high intensities)

The dose response experiments for the current project were carried out with 0% (background control), 6% and 12% settings of laser intensity. In practice, 6% is on the edge of laser intensity required to detect an increase in the number of LR5 responders. As such, 6% should be a useful intensity-setting to detect compound-induced increased sensitivity in the animals. The 12% setting was chosen because this intensity typically gives a robust increase in the number of LR5 responders.

Total Responder speeds, 'LR1 Responder speeds' and 'LR5 Responder speeds' are shown as normalized speeds to allow better comparison between samples. For normalization purposes the average pre-laser speed is set at 1.0 and responder speeds are calculated relative to this value.

The TAV system does not scan/assay the entire testing plate at once. Instead the plate is divided into 21 smaller sections ('Frames') which are assayed on after the other. The order of the 'Frames' for testing remains constant in the XY scan mode ('scanline') used for this project. Note that data collection may continue if less-than-required data are collected in the first 21 'Frames'. This may occasionally lead to resampling of animals that had been tested previously and may have become desensitized to the stimulus.

Finally, no detailed statistical analysis of the results is presented here. For example, using sample sizes of 30 animals, it is not unusual to detect ±10% changes in the percentage of LR5 responders. In general, the tests that were used in this project used several dilution series of compounds and were designed to detect broad overall trends (which could then be tested in further detail).

Dose Responses—Summary of Results (Graphs on Next Two Pages):

(N-Acetyl Carnitine HCl): No obvious effects detected indicating increased sensory sensitivity (even at highest concentration of 8 mM). However, it is noted that in almost all dilution samples (except for NAC2) the percentage of LR5 responders at 6% is similar or higher than at 12%.

(Lipoic Acid): As expected form the OD620 measurements, toxicity is observed at the two highest LA concentrations (this is evident form the 'Frames viewed' (LA1) as well as the overall reduction in speeds in 'Average Speeds' (LA1, LA2)). No obvious effects detected indicating increased sensory sensitivity (even at highest 'non-toxic' concentration of 2 mM). Noted are the relatively low speed of LR1 responders in the LA3 dilution and the relatively high percentage of LR5 responders for dilutions LA4, LA5, LA5 and LA6 (similar to the last DMSO control, which however seems higher than normal).

(Dihydrolipoic Acid): No obvious effects detected indicating increased sensory sensitivity (even at highest concentration of 1:500). It is noted that the second highest concentration (DHLA2) shows a relatively high percentage of LR5 responders at 6% (but see LR5 responder rate at 6% for the second water control

Example 7

Dose Response Testing (3 step)—LC

One 24 well microtiter plate was set up and incubated overnight on the shaker at 20° C. Each well on the plate was set up with 600 L3/L4-stage N2 animals in NGM with a 1:20 dilution of concentrated HB101 *E. coli* (food source) in a volume of 300 µl. Before the animal/HB101 solution was added, test compounds were pipetted into wells. For DMSO controls and compound stocks/dilutions in DMSO (LC) 3 µl was added to each well (1:100 dilutions). No OD620 measurements were taken but the animals were visually scored after 19 h incubation).

Compound distribution on 24 well plate for TAV test:

|   | 1 | 2 | 3 | 4 | 5 | 6 |
|---|---|---|---|---|---|---|
| A |   |   |      | LC3 | DSMO |   |
| B |   |   | DSMO | LC4 |      |   |
| C |   |   | LC1  | LC5 |      |   |
| D |   |   | LC2  | LC6 |      |   |

Visual scoring after 19 h incubation: All wells had cleared (HB101 bacteria removed by growing N2 animals) and most animals had reached adulthood stage with some eggs and L1s in wells (i.e. no toxicity observed).

Dose Responses—setup & general notes on analysis: Same as for other three compounds Dose Responses—Results (Lipoic Acid+N-Acetyl Carnitine conjugate): No obvious effects detected indicating increased sensory sensitivity (even at highest concentration 2 mM).

Example 8

Single Intensity Testing—LA

One 24 well microtiter plate was set up and incubated overnight on the shaker at 20° C. Each well on the plate was set up with 600 L3/L4-stage N2 animals in NGM with a 1:20 dilution of concentrated HB101 *E. coli* (food source) in a volume of 300 µl. Before the animal/HB101 solution was added, test compounds were pipetted into wells. 3 µl each for the DMSO controls and LA dilutions were added to each well (1:100 dilutions). Controls and LA dilutions were done in triplicate (total of 9 wells).

6% Response tests—setup: All 9 wells from the 24 well plate were used for 6% testing and the entire well contents (600 animals) were used for each test. Prior to being placed on the agar plate for TAV testing each sample was processed as described for 'Dose Responses'.

Per plate settings for the dose response experiments were as follows:

| Data collection | | Data analysis | |
|---|---|---|---|
| laser intensity mode: | Constant | min speed limit: | 0.0 |
| laser intensity: | 6% | max speed limit: | 40.0 |
| time collection limit: | 4 minutes | | |
| XY scan mode: | Scanline | | |
| min frame threshold: | 1 | | |
| max frame threshold: | 500 | | |
| firing rounds/frame: | 2 | | |
| min movement ratio: | 2.5 | | |
| max movement ratio: | no limit | | |

Dose Responses—general notes on analysis: Analysis similar as described in 'Dose Responses'. In addition, 'Response ratios' as well as 'A Speed responses' both give measures of how much individual animals changed speed in response to the stimulus (additional information available upon request).

6% Response Test—Results:

(Lipoic Acid): No effects detected indicating increased sensory sensitivity resulting from lipoic acid concentrations of either 2 mM or 1 mM

Example 9

Single Intensity Testing—NAC & DHLA

One 24 well microtiter plate was set up and incubated overnight on the shaker at 20° C. Each well on the plate was set up with 600 L3/L4-stage N2 animals in NGM with a 1:20 dilution of concentrated HB101 *E. coli* (food source) in a volume of 300 µl. Before the animal/HB101 solution was added, test compounds were pipetted into wells. 6 µl each for the water controls and compound dilutions were added to each well (1:50 dilutions). Controls and compound dilutions were done in triplicate (total of 15 wells).

6% Response tests—setup: All 15 wells from the 24 well plate were used for 6% testing) and the entire well contents (600 animals) were used for each test. Prior to being placed on the agar plate for TAV testing each sample was processed as described for 'Dose Responses'.

Per plate settings for the dose response experiments were as follows:

| Data collection | | Data analysis | |
|---|---|---|---|
| laser intensity mode: | constant | min speed limit: | 0.0 |
| laser intensity: | 6% | max speed limit: | 40.0 |
| no. animals collection limit: | 100 | | |
| other settings: | as for LA '6% Response Test' | | |

Dose Responses—general notes on analysis: see 6% Response Tests' for Lipoic acid Dose Responses—Results:

(N-Acetyl carnitine HCl): No effects detected indicating increased sensory sensitivity resulting from N-Acetyl carnitine concentrations of either 8 mM or 4 mM. (Dihydrolipoic acid): No obvious effect detected—such as increased percentage of LR5 responders—at either one of the tested Dihydrolipoic acid concentrations of 1:1,000 or 1:2,500. However, it is noted that with the 1:2,500 concentration, animals that show a LR5 response may be giving a slightly stronger response ('Responder ratios' and 'A Speed responses').

Example 10

Single Intensity Testing—LC

One 24 well microtiter plate was set up and incubated overnight on the shaker at 20° C. Each well on the plate was set up with 600 L3/L4-stage N2 animals in NGM with a 1:20 dilution of concentrated HB101 *E. coli* (food source) in a volume of 300 µl. Before the animal/HB101 solution was added, test compounds were pipetted into wells. 3 µl each for the DMSO controls and LC dilutions were added to each well (1:100 dilutions). Controls and LC dilutions were done in triplicate (total of 9 wells).

6% Response tests—setup: All 9 wells from the 24 well plate were used for 6% testing and the entire well contents (600 animals) were used for each test. Prior to being placed on the agar plate for TAV testing each sample was processed as described for 'Dose Responses'.

| Data collection | | Data analysis | |
|---|---|---|---|
| laser intensity mode: | constant | min speed limit: | 0.0 |
| laser intensity: | 6% | max speed limit: | 40.0 |
| no. animals collection limit: | 100 | | |
| other settings: | as for LA '6% Response Test' | | |

Dose Responses—general notes on analysis: see 6% Response Tests' for Lipoic acid Dose Responses—Results:

(Lipoic Acid+N-Acetyl Carnitine conjugate): No obvious effects detected indicating increased sensory sensitivity resulting from (even at highest concentration 2 mM.

Example 11

Dose Response Testing (11 step)—LC

LC

One 24 well microtiter plate was set up and incubated overnight on the shaker at 20° C. Each well on the plate was set up with 600 L3/L4-stage N2 animals in NGM with a 1:20 dilution of concentrated HB101 *E. coli* (food source) in a volume of 300 µl. Before the animal/HB101 solution was added, test compounds were pipetted into wells. For DMSO controls and compound stocks/dilutions in DMSO (LC) 3 µl was added to each well (1:100 dilutions). No OD620 measurements were taken but the animals were visually scored after 22 h incubation).

Visual scoring after 22 h incubation: All wells had cleared (HB101 bacteria removed by growing N2 animals) and most animals had reached adulthood stage with some eggs and L1s in wells (i.e. no toxicity observed).

Dose Responses—setup & general notes on analysis: Same as for previous dose response experiments except that the data collection settings were modified. Per plate settings for the dose response experiments were as follows:

| Data Collection | | Data analysis | |
|---|---|---|---|
| Laser intensity mode: | :dose response | min speed limit: | 0.0 |
| No. steps | 11 | max speed limit: | 40.0 |
| (laser intensities): | ($0\%_{IO}$ to 100%) | average speed | omitted if <5 |
| Step size: | 10% | calculation: | datapoints |
| Min no. data collect/step: | 10 | | |
| Time collection limit: | 10 minutes | | |
| XY scan mode: | scanline | | |
| Min frame threshold: | 1 | | |
| Max frame threshold: | 500 | | |
| Firing rounds/frame | 2 | | |
| Min movement ratio: | 2.5 | | |
| Max movement ratio: | no limit | | |

Dose Responses—Results:

(Lipoic Acid+N-Acetyl Carnitine conjugate): Possible higher response rate at higher stimulus intensities (speed analysis appears to support this conclusion).

Example 12

Toxicology

Carnitine and alpha-lipoic acid exhibit good tolerability and limited toxicity when administered individually or in combination at high doses to mice and rats. As shown in Patent PCT/IT99/00268, up to 250 mg/kg of acetyl L-carnitine or 100 mg/kg of alpha-lipoic acids can be parenterally administered to these animals. With a carnitine mixture (acetyl L-carnitine, propionyl L-carnitine, isovaleryl L-carnitine combined in a 1:1 weight ratio to one another), these animals tolerate (without dying) the following administered orally: 250 mg/kg carnitine mixture plus more that 500 mg/kg of acetyl L-carnitine; or 500 mg/kg carnitine mixture plus 200 mg/kg of alpha-lipoic acid. Also, prolonged administration via the diet for 30 consecutive days, of 200 mg/kg of acetyl L-carnitine or of 200 mg/kg carnitine mixture together with 100 mg/kg of alpha lipoic acid was well tolerated and lead to no signs of toxicity.

Example 13

Carnitine in Rodents (IIa) Acetyl-L-Carnitine Eliminates Sensory Neuronal Loss after Peripheral Axotomy in Rat
    This experiment was described in:
    Systemic acetyl-L-carnitine eliminates sensory neuronal loss after peripheral axotomy: a new clinical approach in the management of peripheral nerve trauma. A. M. Hart, M. Wiberg, M. Youle, and G. Terenghi *Exp. Brain Res* (2002) 145:182-189.
Methods
    Adult rats underwent unilateral sciatic nerve division at the upper boarder of quadratus femoris. Parenternal systemic therapy with acetyl-L-carnitine in sterile normal saline was commenced in the immediate postoperative period as follows (group n=6): "high dose treatment" group(s) received 50 mg/kg/day; "low dose treatment" group received 10 mg/kg/day; "sham treatment" group received an equivalent volume of normal saline; and "no treatment" group(s) received no treatment.
    At either 2 weeks or 2 months after axotomy, L4 and L5 dorsal root ganglia were harvested bilaterally and postfixed. As described in Hart et al *Exp. Brain Res* (2002) 145:182-189, neuronal death was quantified with a combination of TUNEL [TdT (terminal deoxyribonucleotidyl transferase) uptake nick end labeling] and neuron counts were obtained using the optical disection technique (Gundersen et al 1988).
Results
    Sham treatment had no effect upon neuronal death. Acetyl-L-carnitine treatment caused a large reduction in the number of TUNEL-positive neurons 2 weeks after axotomy (sham 33/group; low-dose 6/group, P=0.132; high-dose 3/group, P<0.05), and almost eliminated neuron loss (sham 21%; low-dose 0%, P=0.007; high-dose 2%, P<0.013). Two months after axotomy the neuroprotective effect of high-dose treatment was preserved for both TUNEL counts (no treatment five/group; high-dose one/group) and neuron loss (no treatment 35%; high-dose −4%, P<0.001).
    Systemic treatment with ALCAR (50 mg/kg/day) significantly reduced both the number of TUNEL positive neurons and the neuron loss found 2 weeks after peripheral axotomy. Neuronal death was prevented, rather than just delayed, since this protective effect was found to be preserved 2 months after taxonomy, by which time neuron loss has effectively. These results suggest that acetyl-L-carnitine may be suitable for clinical use in the prevention of neuronal death after peripheral nerve trauma.

Example 14

Acetyl-L-carnitine Enhances Peripheral Nerve Regeneration in Rat

This experiment was described in:
    Pharmacological enhancement of peripheral nerve regeneration in the rat by systemic acetyl-L-carnitine treatment (A. M. Hart, M. Wiberg, G. Terenghi, Neuroscience *Letters* 334 (2002) 181-185).
Methods
    Adult rats underwent unilateral sciatic nerve division at the upper border of quadratus femoris. Two months later, (once sensory neuron loss had stabilized), 1 cm nerve graft repairs were performed on the rats. One group (group n=5) was then treated with 50 mg/kg/day acetyl-L-carnitine by daily intraperitoneal injection for 6 weeks until harvest, while a control group did not receive treatment. Regeneration area and distance were determined by quantitative immunohistochemistry.
Results
    Acetyl-L-carnitine treatment significantly increased immunostaining for both nerve fibres (total area 264% increase, P<0.001; percentage area 229% increase, P<0.001), and Schwann cells (total area 111% increase, P<0.05; percentage area 86% increase, P<0.05), when compared to no treatment. Regeneration into the distal stump was greatly enhanced (total area 2,242% increase, P=0.008; percentage area 3,034% increase, P=0.008).
    Acetyl-L-carnitine significantly enhances the regenerative capacity of neurons that survive peripheral nerve trauma, independently of Acetyl-L-carnitine's neuroprotective effect of increasing the number of neurons surviving peripheral axotomy.

Example 15

Acetyl-L Carnitine to Treat Noise-Induced Hearing and Auditory Hair Cell Loss in Chinchilla This experiment was described in:
    Enhanced Intrinsic Cochlear Defences to Reduce Noise-Induced Hearing Loss, R. D. Kopke, J. K. Colemna, J. Liu, K. C. Camplell and R. H. Riffenburgh (2002) *Laryngoscope* 112(9):1515-1532.
Methods
    Adult chinchilla laniger, having baseline-hearing thresholds determined by auditory brainstem response (ABR) recording, received injections of saline or saline plus active experiment compound starting before and continuing after a 6-hour 105 dB continuous 4-kHx octave band noise exposure. ABRs were obtained immediately after noise exposure and weekly for 3 weeks. After euthanization, cochlear hair cell counts were obtained and analyzed.
Results
    Acetyl-L carnitine administration reduced noise-induced threshold shifts. Three weeks after noise exposure, no threshold shift at 2 to 4 kHz and <10 dB threshold shifts were seen as 6 to 8 kHz in acetyl-L-carnitine treated animals compared with 30 to 35 dB threshold shifts in control animals,
    Acetyl-L-carnitine treatment reduced both inner and outer hair cell loss. Outer hair cell loss averaged <10% for the 4- to 10-kHz region in Acetyl-L carnitine treated animals and 60% in the same region of saline injects-noise-exposed control animals.

Acetyl-L carnitine has a protective effect on impulse noise induced cochlear damage.

Example 16

Effect of L-Acetyl-Carnitine on Subcutaneous Adipocytes in Rats

This experiment was described in:
The aging process of skin and the increase in size of subcutaneous adipocytes, P. Baldassarri and M. Calvani (1994) *Int. J. React.* 16(5-6):229-41
Results
Long-term administration of L-acetyl-carnitine blocks progressive increase in size of subcutaneous adipocytes present in rat's aging skin.
(IVe) The Effects of Carnitine on Random Pattern Flap Survival in Rats
This experiment was described in:
The Effects of Carnitine on Random Pattern Flap Survival in Rats (2001) A. Teoman Tellioglu et al., *Plastic & Reconstructive Surgery* 108(4):959-963
Methods
30 rats had their dorsal elevated skin flaps elevated and were divided into 3 groups (n-10) Group 1 and 2 respectively received 50 and 100 mg/kg/day carntinte for 1 week. Group 3 (control) received none.
Results
Areas of skin flap necrosis for groups 1, 2 and 3 three respectively were 12.55, 9.23 and 4.9 cm$^2$. Carnitine treated groups had a statistically significant improvement of flap necrosis compared to control (group 2, p=0.001, group 3 p=0.000)

Example 17

Alpha-Lipoic Acid in Rodent Models (IIa) Alpha-Lipoic Acid for Treating Nerve and Vascular Dysfunction in Diabetic Rats
This experiment was described in:
Effects of antioxidants on nerve and vascular dysfunction in experimental diabetes (N. E., Cameron and M. A. Cotter, *Diabetes Research and Clinical, Practice* 45 (1999) 137-146)
Reduced peripheral nerve perfusion causing endoneurial hypoxia is a factor in causing diabetic neuropathy. Sciatic nerve blood flow is reduced in streptozotocin-induced diabetic rats. Antioxidants, such as α-lipoic acid, may improve measures of nerve function, such as nerve conduction velocity (NCV) at least in part by improving or preventing blood flow defects.
Six weeks after undergoing streptozotocin diabetes induction, rats were given α-lipoic acid (20 mg/kg/day) for two week followed by testing. These rats showed improved (a) sciatic endoneutral blood flow and (b) sciatic motor nerve NCV over diabetic rats not given α-lipoic acid.

Example 18

Carnitine & Alpha-Lipoic Acid Together in Rodents (IVa) Treatment with Acetyl L-Carnitine, a Carnitine Mixture, Alpha-Lipoic Acid, or Combinations of these Products, Improve Sciatic Nerve Regeneration in Diabetic Rats.

This experiment was described in patent PCT/IT99/00268
Methods
The technique used is as described in Fernandez (Fernandez E., *Int. J. Clin. Pharmacol. Res.* 10, 85, 1990). Briefly, diabetes (serum glucose above 450 mg/ml) was induced in rats by intravenous injection of 100 mg/kg alloxan. Diabetic rats have reduced ability to regenerate peripheral nerves compared to controls. Acetyl L-carnitine, a carnitine mixture (acetyl L-carnitine+propionyl L-carnitine+isovaleryl L-carnitine in a 1:1 weight ration to one another), α-lipoic acid, or combinations of these were administered in diet in such that daily intake was 200 mg/kg Acetyl L-carnitine, 200 mg/kg carnitine mixture and 50 mg/kg of α-lipoic acid. The compounds were administered for seven day prior to and thirty days after sciatic nerve cutting. Under anaesthesia 1 cm of the sciatic nerve was exposed and a cut made at the sciatic foramen. An epineural suture marked the lesion border. Thirty days after cutting rats were sacrificed and tibia nerve tissue was examined for number and density of degenerate elements.
Result
Acetyl L-carnitine, a carnitine mixture, α-lipoic acid, or combinations of these all help prevent diabetic damage to nerve regeneration. The greatest effect was from carnitine(s) and α-lipoic acid acting synergistically together.
The table shows number and density of tibial nerve degenerate elements after sciatic nerve cutting in diabetic rat.

| Treatment | Number | Density (per 100 nm$^2$) |
| --- | --- | --- |
| Control | 965 ± 141 | 0.31 ± 0.04 |
| Acetyl L-carnitine | 560 ± 61 | 0.16 ± 0.02 |
| Carnitine mixture | 520 ± 55 | 0.14 ± 0.02 |
| α-lipoic acid | 590 ± 0.70 | 0.20 ± 0.04 |
| Acetyl L-carnitine + α-lipoic acid | 340 ± 0.41 | 0.10 ± 0.01 |
| Carnitine mixture + α-lipoic acid | 360 ± 0.55 | 0.11 ± 0.02 |

Example 19

Treatment with Acetyl L-carnitine, a Carnitine Mixture, Alpha-Lipoic Acid, or Combinations of these Improve Neuromuscular Conduction (NMCV) in Diabetic Rats This experiment was described in patent PCT/IT99/00268.
NMCV slowing is a characteristic of peripheral neuropathies, including diabetic neuropathy, which can be improved by Acetyl L-carnitine, a carnitine mixture, α-lipoic acid, or combinations of these.
The technique used is as described in Fernandez (Fernandez, E., *Int. J. Clin. Pharmacol. Res.* 10, 85, 1990). Diabetes (serum glucose above 450 mg/ml) was induced in rats by intravenous injection of 50 mg/kg streptozocin. Sciatic nerve NMCV in these diabetic rats was measured as described in PCT/IT99/00268. PCT/IT99/00268 does not specify amount or product administered)
PCT/IT99/00268 shows neuromuscular conduction test in the diabetic rat.

| Treatment | NMCV (m/sec)r |
| --- | --- |
| Control | 42.2 ± 2.4 |
| Diabetics + acetyl L-carnitine | 34.5 ± 2.1 |

-continued

| Treatment | NMCV (m/sec)r |
|---|---|
| Diabetics + carnitine mixture | 38.5 ± 1.9 |
| Diabetics + α-lipoic acid | 39.9 ± 2.1 |
| Diabetics + acetyl L-carnitine + α-lipoic acid | 40.1 ± 1.5 |
| Diabetics + carnitine mixture + α-lipoic acid | 42.0 ± 3.1 |

Example 20

Treatment with Acetyl L-carnitine, a Carnitine Mixture, Alpha-Lipoic Acid, or Combinations of these Improve Motor Co-ordination in "Wobbler Mice"

This experiment was described in patent PCT/IT99/00268

"Wobbler" mice have motor problems due to progressive atrophy of motoneurons and of musculocutaneous nerve fibers. Motor control tests as described in Mitsumotot H., *Anal. Neurol.* 36, 14, 1994) were conducted on Wobbler mice after twenty days oral treatment with Acetyl L-carnitine (200 mg/kg), carnitine mixture (200 mg/kg), α-lipoic acid (50 mg/kg), or combinations of these. Treatment improved the running time for these animals. The combination of carnitine and α-lipoic acid having a synergistic effect.

PCT/IT99/00268 shows % increase in running time

| Control | 55 ± 4.5 |
|---|---|
| Acetyl L-carnitine | 35 ± 3.2 |
| carnitine mixture | 38 ± 4.1 |
| α-lipoic acid | 40 ± 3.9 |
| Acetyl L-carnitine + α-lipoic acid | 20 ± 1.9 |
| Carnitine mixture + α-lipoic acid | 26 ± 2.1 |

Example 21

Treatment with Acetyl L-Carnitine, a Carnitine Mixture, α-Lipoic Acid, or Combinations of these Improve Cisplatin-Induced Sensory Neuronal Sessions in Rat This experiment was described in patent PCT/IT99/00268

For seven days, rats were subcutaneously injected with 10 mg/kg cisplatin alone, or in combination with 300 mg/kg Acetyl L-carnitine administered orally, 300 mg/kg carnitine mixture orally, 50 mg/kg α-lipoic acid orally, or combinations of these products. Sensory perception abnormalities were tested as in (Apfel, S. C. *Ann. Neurol.* 29, 89, 1991). Carnitine and α-lipoic acid acted synergistically to have the greatest effect.

| Cisolatin | Treatment | Equilibrium time (sec) |
|---|---|---|
| n/a | Control | 4.8 ± 1.4 |
| Cisplatin | n/a | 8.4 ± 0.8 |
| Cisplatin | acetyl L-carnitine | 9.5 ± 0/6 |
| Cisplatin | carnitine mixture | 8.9 ± 0.6 |
| Cisplatin | α-lipoic acid | 9.9 ± 0.8 |
| Cisplatin | acetyl L-carnitine + α-lipoic acid | 14.4 ± 1.8 |
| Cisplatin | carnitine mixture + α-lipoic acid | 13.8 ± 2.1 |

Example 22

Carnitine in Humans (Va) Acetyl-L-Carnitine in Treatment of Diabetic Neuropathy in Humans.

This experiment was described in:
Acetyl-L-Carnitine (Levacecarnine) in the treatment of Diabetic Neuropathy: a Long-Term, Randomized, Double-Blind Placebo-Controlled Study (De Grandis D., Minardi, C., *Drugs in R & D,* 2002, vol. 3, no. 4 pp. 223-231 (9) (note we only have abstract)

Thirty-three patients having diabetic neuropathy were treated with acetyl-L-carnitine (or placebo), administered intramuscularly at a dosage of 1000 mg/day for 10 days and subsequently continued orally at a dosage of 2000 mg/day for 355 days. Acetyl-L-carnitine was well tolerated over the 12 month period of this study.

Patients receiving acetyl-L-carnitine showed a statistically significant improvement in nerve conduction velocity NCV at 6- and 12 months and a significant reduction in pain. Effectiveness on Pain was measured via visual analogue scale (VAS).

Of the 294 patients with impaired electrophysiological parameters at baselines, those treated with acetyl-L-carnitine showed at 12 months a statistically significant improvement in mean NCV, Amplitude and VAC pain score compared to placebo.

Example 23

L-Propionyl Carnitine in Treatment of Chronic Critical Limb Ischaemia in Humans

This experiment was described in:
Efficacy of L-Propionyl Carnitine in treatment of Chronic Critical Limb Ischaemia. S. S. Signorelli, L. Di Pino, M. P. Costa, D. Digrandi, G. Pennisi and G. Marchese (2001) *Clinical Drug Investigation*, vol. 21, no. 8 pp. 555-561(7)

Methods 188 patients were treated. 85 had a recent (within previous 15 days) reduction in pain free walking distance (PWD), 59 had rest pain lasting for ≧2 weeks, and 44 patients had skin ulcers appearing within the previous 15 days.

For two weeks, patients received intravenous infusion of 1.2 g/day L-Propionyl Carnitine and also received calcium heparin 25,000 U/day (12,500 U twice daily) subcutaneously.

Results

Treatment resulted in statistically significant improvements over baseline: 78% increase in mean PWD (p<0.001); 83% decrease in mean pain score (p<0.001); and 48% decrease in mean ulcer size (diameter) (p<0.001)

L-propionyl carnitine appears to be a promising treatment for patients with peripheral arterial disease.

Example 24

L-Propionyl Carnitine Protects Tissues from Ischaemic Injury in Human

This experiment was described in:
L-Propionyl Carnitine Protects Tissues form Ischaemic Injury in an "In Vivo" Human Ischeamia-Reperfusion Model in Humans G. M. Andreozzi, R. Martini, R. M. Cordova and A., D'Eri (2002) *Clinical Drug Investigation* vol. 22, no supplement 1, pp. 15-21(7).

Methods 16 male patients with intermediate claudication (mean absolute claudatin distance 193.19±51.51M) received intravenous infusion 600 mg L-propionyl carnitine.

Laser-Doppler perfusion units and power spectrum, transcutaneous oxygen pressure (TcPO) and transcutaneous carbon dioxide pressure (TcPCO) were measured at baseline, during ischaemia (which was induced by means of an inflated pneumatic cuff wrapped around the calf) and during reperfusion, before and after L-propionyl carnitine infusion.

Results

Perfusion units and TcPO did not change significantly after L-propionyl carnitine compared to pre-treatment values.

Mean laser—Doppler power spectrum, which was 0.20 units at rest and 1.13 during reperfusion before treatment, increased significantly to 0.89 and 2.24 respectively, after L-propionyl carnitine infusion (p=0.01 and P=0.00074, respectively, vs pre-treatment values).

L-propionyl carnitine had no significant effects on resting TcPCO, but induced a significant decrease in TcPCO measured at hypoxia point (96.9 m Hg before treatment vs 90.2 mm Hg after treatment; p=0.0001) and during reperfusion (115.9 vs 103.5 mm Hg, respectively; p=0.0006)

L-propionyl carnitine protects tissue from ischemic injury by improving arteriol function and reducing acidosis, without affecting arterial inflow, suggesting potential use in other stages of peripheral arterial disease and in patients undergoing surgery.

Example 25

Alpha-Lipoic Acid in Humans (VIa) Alpha-Lipoic Acid for Treating Diabetic Polyneuropathy Humans This experiment was referred to in:

"New Drugs to Prevent or Treat Diabetic Polyneuropathy" D. Ziegler, *International Diabetes Monitor* 13, No 3, 2001 but note there was no reference naming the particular studies

Five randomized placebo-controlled clinical trials have been published suggesting: a) short term treatment for 3 weeks using 600 mg α-lipoic acid i.v. per day appears to reduce pain, paraethesia and numbness, and to improve neuropathic defects; b) subsequent oral treatment for 4-7 months reduces neuropathic defects an improves cardiac autonomic neuropathy.

We claim:

1. A compound consisting of carnitine, lipoic acid, and an ethylene linker linking said carnitine with said lipoic acid.

2. A composition comprising the compound of claim 1.

3. The compound of claim 1, wherein said linker is stable at a pH of 7.4 and is hydrolysable (acid cleavable) at a pH of less than 6.

4. The method of using the compound of claim 1 for increasing cellular metabolism while simultaneously alleviating oxidative stress in a mammal.

5. A compound consisting essentially of

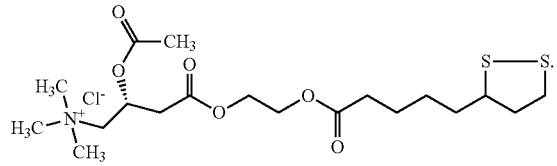

4

* * * * *